(12) United States Patent
Gillespie

(10) Patent No.: US 9,955,718 B2
(45) Date of Patent: *May 1, 2018

(54) METHODS AND PRODUCTS TO PROVIDE ORAL NUTRITIONAL CARE TO SUBJECTS WITH DEMENTIA

(71) Applicant: D&E Gillespie Enterprises LLC, Coatesville, PA (US)

(72) Inventor: John Gillespie, Coatesville, PA (US)

(73) Assignee: D&E Gillespie Enterprises LLC, Coatsville, PA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/140,213

(22) Filed: Apr. 27, 2016

(65) Prior Publication Data
US 2016/0242451 A1    Aug. 25, 2016

Related U.S. Application Data

(63) Continuation of application No. 14/304,802, filed on Jun. 13, 2014.

(60) Provisional application No. 61/834,429, filed on Jun. 13, 2013.

(51) Int. Cl.

| | |
|---|---|
| A23L 23/00 | (2016.01) |
| A23L 33/15 | (2016.01) |
| A61K 31/122 | (2006.01) |
| A61K 31/07 | (2006.01) |
| A61K 31/375 | (2006.01) |
| A61K 31/355 | (2006.01) |
| A61K 33/04 | (2006.01) |
| A61K 45/06 | (2006.01) |
| A61K 31/197 | (2006.01) |
| A61K 31/202 | (2006.01) |
| A61K 31/4415 | (2006.01) |
| A61K 31/519 | (2006.01) |
| A61K 31/522 | (2006.01) |
| A61K 31/575 | (2006.01) |
| A61K 31/593 | (2006.01) |
| A61K 31/714 | (2006.01) |
| A61K 33/00 | (2006.01) |
| A61K 33/26 | (2006.01) |
| A61K 33/30 | (2006.01) |
| A61K 33/32 | (2006.01) |
| A61K 33/34 | (2006.01) |
| A61K 33/42 | (2006.01) |
| A23L 33/00 | (2016.01) |
| A23L 33/12 | (2016.01) |
| A23L 33/16 | (2016.01) |
| A61K 35/12 | (2015.01) |
| A61K 36/00 | (2006.01) |

(52) U.S. Cl.
CPC ............... *A23L 33/15* (2016.08); *A23L 23/00* (2016.08); *A23L 33/12* (2016.08); *A23L 33/16* (2016.08); *A23L 33/40* (2016.08); *A61K 31/07* (2013.01); *A61K 31/122* (2013.01); *A61K 31/197* (2013.01); *A61K 31/202* (2013.01); *A61K 31/355* (2013.01); *A61K 31/375* (2013.01); *A61K 31/4415* (2013.01); *A61K 31/519* (2013.01); *A61K 31/522* (2013.01); *A61K 31/575* (2013.01); *A61K 31/593* (2013.01); *A61K 31/714* (2013.01); *A61K 33/00* (2013.01); *A61K 33/04* (2013.01); *A61K 33/26* (2013.01); *A61K 33/30* (2013.01); *A61K 33/32* (2013.01); *A61K 33/34* (2013.01); *A61K 33/42* (2013.01); *A61K 35/12* (2013.01); *A61K 45/06* (2013.01); *A23V 2002/00* (2013.01); *A61K 36/00* (2013.01)

(58) Field of Classification Search
CPC ...................................................... A23L 23/00
See application file for complete search history.

(56) References Cited

PUBLICATIONS

Singh et al., "Development of the Mediterranean soup for enteral nutrition and for prevention of cardiovascular disease," The Open Nutraceutical Journal 5(Suppl 1-M7):90-98, 2012.*
Al-Jasass et al. ("Chemical composition and fatty acid content of some spices and herbs under Saudi Arabia conditions," The Scientific World Journal, vol. 2012, article No. 859892, 5 pp., 2012.*

* cited by examiner

*Primary Examiner* — Rosanne Kosson
(74) *Attorney, Agent, or Firm* — The Fedde Law Firm; Kenton Fedde; Nathaniel Fedde

(57) ABSTRACT

The present invention provides food products, nutritional programs, and methods for meeting nutritional needs of subjects with dementia and related cognitive disorders. In one embodiment, the invention provides a food product comprising a reversibly sealed container and a soup, wherein the soup is in the container and comprises a total volume of 200-2000 mls, a vegetable or meat component, 300 to 2500 calories, a macronutrient caloric distribution comprising: 20-80% fat, 10-45% protein, and 10-65% carbohydrate, about 2% to about 40% medium chain triglycerides, omega 3 fatty acids in an amount of 100 to 2000 mg and less than 20 solid food particles having a volume greater than about 20 cm$^3$. Such food products, when administered to affected subjects, can positively impact (i) nutritional status; (ii) quality of life; (iii) disease course; (v) the demand for assistance from a care giver; (vi) subject compliance with a nutritional plan using the food product, and (vii) ease of monitoring compliance by the caregiver for verification.

24 Claims, No Drawings

METHODS AND PRODUCTS TO PROVIDE ORAL NUTRITIONAL CARE TO SUBJECTS WITH DEMENTIA

CROSS-REFERENCE TO RELATED APPLICATIONS

This application is a continuation of U.S. patent application Ser. No. 14/304,802 filed 13 Jun. 2014, which claims the benefit of U.S. provisional patent application Ser. No. 61/834,429 filed 13 Jun. 2013, which are each incorporated herein by reference in its entirety.

TECHNICAL FIELD

The present invention relates to methods and products for providing oral nutritional care to subjects with dementia.

BACKGROUND OF THE INVENTION

Dementia is a group of disorders characterized by loss of integrated central nervous system functions, resulting in a diminished ability to understand concepts or instructions, to store and retrieve information into memory, and in behavioral and personality changes.

A reduction in memory and cognitive function is considered to be a normal consequence of aging in humans. Age-related cognitive decline is a term used to describe objective memory decline in the elderly who have cognitive functioning that is normal relative to their age peers. Age-related cognitive decline is different from Mild Cognitive Impairment (MCI) that is more severe or consistent, and may indicate the early stages of a condition such as dementia (APA Presidential Task Force on the Assessment of Age-Consistent Memory Decline and Dementia, February 1998).

The most prevalent forms of dementia in the United States are Alzheimer's Disease (40 to 60% of diagnoses); Vascular Dementia (10 to 20% of all diagnoses); Mixed Dementia (10% of all diagnoses); Dementia with Lewy Bodies (10% of all diagnoses). Secondary dementias caused by drugs, delirium, or depression represent 5% or less of all dementia diagnoses in the United States. Alzheimer's disease (AD) is classified as dementia with neurodegeneration, and is prevalent worldwide. Senile dementia itself refers to all dementia in the population age 65 and over and includes AD.

One of the challenges among all forms of dementia is the ability of self care. Even with regular support of a family member/caregiver, nutritional homeostasis is difficult to maintain. Providing adequate nutrition to these subjects is especially challenging by the very nature of typical manifestations, namely: loss of appetite, lack of recognition of food preparations, confusion about appropriate quantities of food intake, loss of smell, forgetting to eat, and difficulty with following cooking/preparation/eating directions.

There is a need in the art for nutritional products and nutritional plans that can help maintain nutritional homeostasis in dementia subjects while minimizing requirement for living assistance.

SUMMARY OF THE INVENTION

It has now been discovered that food products of the present invention can be administered to dementia subjects and can positively impact (i) nutritional status; (ii) quality of life; (iii) pathophysiology of the dementia; (iv) disease course; (v) the demand of assistance from a care giver; and (vi) ease of monitoring compliance by the caregiver for verification.

The present invention provides methods and products to supply a substantial portion of a subject's daily nutritional needs.

In one embodiment, the invention provides a food product comprising a soup, wherein the soup comprises:
200 ml to 2000 ml of water;
a vegetable or meat component;
300 to 2500 calories; and
a macronutrient caloric distribution comprising:
  20-80% fat;
  10-45% protein; and
  10-65% carbohydrate.

Optionally, the Soup further comprises antioxidant in an amount of 100 to 500 mg equivalents of vitamin C as calculated by FRSA (defined herein).

Optionally, the Soup (in any of the embodiments) further comprises omega 3 fatty acids in an amount of 100 to 2000 mg.

Optionally, the Soup (in any of the embodiments) further comprises fiber in an amount of 2.5 to 30 gm.

Optionally, the Soup (in any of the embodiments) further comprises cholesterol in an amount of 0 to 250 mg.

Optionally, the Soup (in any of the embodiments) comprises medium chain triglycerides in an amount of about 2% to about 40% of total calories or about 10% to about 50% of the fat calories.

Optionally, the Soup contains each of the above components in amounts set forth above, that is, 200 ml to 2000 ml of water; a vegetable or meat component; 300 to 2500 calories; a macronutrient caloric distribution comprising: 20-80% fat; 10-45% protein; and 10-65% carbohydrate, antioxidant in an amount of 100 to 500 mg equivalents of vitamin C, omega 3 fatty acids in an amount of 100 to 2000 mg, fiber in an amount of 2.5 to 30 gm, cholesterol in an amount of 0 to 250 mg, medium chain triglycerides in an amount of about 2% to about 40% of total calories or about 10% to about 50% of the fat calories. Optionally, the Soup further comprises a substantial amount of vitamins, anti-dementia agents, and odiferous components.

Optionally, the Soup (in any of the embodiments) is a small-particle Soup.

Optionally, the food product comprises a Soup in an easy-open closed container. Optionally, the container is a microwavable container. Optionally, the container provides some visually recognizable features indicative of a food container (e.g. in the shape of a soup bowl or with a picture or drawing of a soup bowl).

The invention also provides a kit comprising a plurality of food products.

The invention also provides a method of administering a Soup of the invention to a dementia subject. Optionally, the administration is self-administration.

DETAILED DESCRIPTION OF THE INVENTION

As used here, the following definitions and abbreviations apply.

"Caregiver demand" refers to the burden for and on a caregiver. Demand can be quantified not only in objective terms such as in the number of hours each day or week but also in subjective terms such as caregiving difficulty, global caregiver strain, tension, depression, anger, fatigue, vigor, confusion, and total mood disturbance. For example, The Preparedness for Caregiving Scale (Archbold, Stewart, Greenlick, & Harvath, 1990) is a caregiver self-rated instrument that consists of eight items that asks caregivers how well prepared they believe they are for multiple domains of caregiving (e.g. roles such as providing physical care, providing emotional support, setting up in-home support services, and dealing with the stress of caregiving).

"Concentration", when expressed as a percentage, means weight/weight (w/w).

"$D_{90}$" means a diameter value for which 90% of the solid food particles are smaller.

"Dementia subjects" means individuals or populations of individuals with dementia of any form and specifically includes Alzheimer's disease, vascular dementia, mixed dementia, dementia with Lewy bodies, secondary dementias (e.g. caused by drugs, delirium, or depression). "Dementia subjects" also include individuals and populations with age-related cognitive decline and individuals and populations with mild cognitive Impairment. "Dementia subjects" further includes a number of conditions including autism and certain intelligence deficiencies with Alzheimer's-like eating-related deficiencies. "Dementia subjects" also includes subjects with mild cognitive impairment (or incipient dementia or isolated memory impairment), e.g. subjects at a transitional stage between normal aging and dementia.

"Daily nutritional needs (or "DNN") refers to nutritional requirements for dementia subjects in terms of calories and certain macronutrients (e.g. fat, fiber, sugar, saturated fatty acids) and micronutrients (e.g. vitamin D. calcium, folate). DNN values, as used here, can refer to theoretical values taken from the literature and may be adjusted according to the subject's gender, age, physical activity, as well as genetic, environmental, and physical factors. DNN values can also be drawn from those published by professional societies. For example, the dietary reference intakes (DRIs) for nutrients are values established by the Food and Nutrition Board (FNB) of the Institute of Medicine, National Academy of Sciences, that encompass the estimated average requirement (EAR), the recommended dietary allowance (RDA), the adequate intake (AI), and the tolerable upper intake level (UL).

"Easy-open" refers to a container that can be opened without a sharp object or a cutting device (such as a can opener). Optionally, an easy open container can be opened without requiring above average strength, or without a complicated, multistep process. Optionally, an easy-open container is configured to be opened by hand without the use of a tool.

"Exemplary" (or "e.g." or "by example") means a non-limiting example.

"Macronutrient caloric distribution" means the distribution of calories among the macronutrients.

"Quality of life" (or "QoL") is a reference to the general well-being of dementia subjects or their caregivers. There are a number of quantitative assessments of QoL: One such example is the Wisconsin Quality of Life Index (W-QLI) which is based upon a client questionnaire that reflects the personal priorities and goals of individual mental health clients and probes 1) general life satisfaction, 2) activities and occupations, 3) psychological well-being, 4) physical health, 5) social relations/support, 6) economics, 7) activities of daily living, 8) symptoms, and 9) goal attainment. Each domain is individually weighted depending on its relative importance to the patient. HRQoL is a health related QoL assessment and can be any HRQoL such as he SF-36, the NHP, the QL-I, the WHOQOL-BREF, the WHODASII, the EQ-5D, and the Q-LES Q (Quality of Life, Enjoyment and Satisfaction Questionnaire).

"Soup" (in uppercase "S") means a soup of the present invention.

"Subject compliance", as used here, means compliance of a dementia subject with the present nutritional plan; e.g. generally consuming the directed amounts of the directed Soup at the directed time and in the directed manner.

"Tbs" means tablespoon or 15 mls.

"Tsp" means teaspoon or 5 mls.

"$V_{90}$" means a volume value for which 90% of the solid food particles are smaller.

Dementia Subjects

The food products, packaged food products (e.g. food product in a container), kits, and nutritional plans, according to the present invention, are useful for any dementia subjects. While the pathophysiology of dementia is heterogeneous among the group of dementia disorders, a commonality of symptoms make the present invention widely useful for dementia subjects. For example, there are Autism variants that have difficulty self-administering nutrition (e.g., struggle with instructions; forget what has been consumed, etc.). Traumatic brain injury can lead to cognitive changes typical of Alzheimers (e.g. changes in personality, emotional problems, and difficulty making decisions or solving problems) and may increase a person's risk for developing dementia. Indeed, Alzheimer's-like symptoms, as they apply to nutrition, are not atypical in individuals that are in the educable or trainable range of intelligence but exhibit a moderate or severe mental deficiency. Depression can also cause such symptoms.

Through insight of the inventor, it has been concluded that the nutritional challenges of dementia subjects result from the interaction of a number of defective mental processes—and that the nutritional challenge can be remarkably met by the present invention.

Without being bound by theory, it is believed that many dementia subjects fail to recognize what they are eating and that such lack of recognition can account for some of the unwillingness to eat. Moreover, the lack of recognition can contribute to lack of appetite stimulation. As discussed below, due to the interaction of a number of features, the Soup of the present invention is recognized remarkably well by dementia subjects and stimulates appetite (and subject compliance with the present nutritional plan).

Dementia subjects, irrespective of the cause, are typically confounded by decisions. Unexpected success of the present invention can be due, in part, to the relative simplicity and ease of self-administration by dementia subjects.

Through empirical observation, the inventor has concluded that a spoon and a bowl of soup are recognized and eaten by dementia subjects more readily than any other food substance examined. Without being bound by theory, the inventor speculates that while a fork can be used in several different ways for different kinds of food substances, a spoon in generally used only one way and for fluid substances (e.g. soup). Indeed, the very notion of a "soup spoon" reinforces its identification and its use. Again, through insight of the inventor, it has been discovered that while some features of the present invention may have been used in the past, when combined as taught herein, they have more than a predicted positive effect.

Soup

The present invention provides a food product comprising water and a food component ("Soup"). The Soup comprises at least one vegetable or meat component. Optionally, the Soup comprises solid food particles.

Optionally, the Soup comprises a liquid phase comprising at least one food component mixed with water, wherein the at least one food component comprises a nutritional or caloric substance. Optionally, the at least one food component is a liquid food component (e.g. oil), or food substance dispersed in the liquid phase (e.g. dissolved particles, suspended microscopic particles, food particles in a colloidal mixture, or substances extracted from a steeped solid food component). Examples of useful nutritional or caloric substances that can be included in a liquid phase include vitamins, elements, anti-dementia agents, anti-oxidants, fiber, odiferous components, carbohydrates, fats, and proteins, e.g. those herein.

The Soup comprises solid food particles (e.g. vegetables or meats). The solid food particles of the Soup can be further blended, pulverized, puréed, etc.

Optionally, the Soup comprises a starchy vegetable (e.g. grain such as rice or grain product such as pasta).

Optionally, the Soup comprises a tomato product (e.g. tomato paste, tomato sauce, tomato soup, tomato extraction, or tomato pieces).

Optionally, the Soup comprises any of:
a. a starchy vegetable and a meat;
b. a starchy vegetable and a non-starchy vegetable
c. a meat and a non-starchy vegetable; and
d. a starchy vegetable, a non-starchy vegetable, and a meat.

An exemplary Soup comprises 190 ml to 2500 ml of water, a vegetable or meat component, and 300 to 2000 calories.

A Soup of the present invention can be in any form. Optionally, the Soup is a homogenous mixture or a heterogeneous mixture. Optionally, the Soup is in a form selected from: a dispersion, a solution, a suspension, and a colloid.

Optionally, the Soup comprises one or more solid food particles that are suspended in water (e.g. suspended grains). Alternatively, the Soup can comprise one or more solid food particles that are not suspended by the water (e.g. meat chunks that sink to the bottom of the Soup). Optionally, the Soup comprises one or more solid food particles that are suspended in water and one or more solid food particles that are not suspended.

Optionally, the Soup comprises a mixture of water and a solid meat or vegetable component. Optionally, the Soup comprises nutrients in the water extracted or leeched from the solid meat or vegetable component.

Optionally, the Soup is made by heating a mixture of water and a meat or vegetable component. Optionally, heating comprises boiling.

A Soup of the invention can, for example, have distinctive properties of a food typically referred to as "soup" by those skilled in the culinary arts.

Components
Solid Food Particles: Small Particle Soups

The present Soup can be formulated for easy consumption. In one embodiment, the Soup is formulated with a small food particle size or as a drinkable dispersion with or without food particles ("small particle Soup"). Accordingly, such small-particle Soups optionally have particle sizes that can be typically consumed without cutting into smaller pieces, without hanging off the spoon excessively, without causing oral pain or difficulty due to poor dentition, and with negligible risk of choking. It has surprisingly been discovered here that the size of solid food substance in the present Soup contributes significantly to subject compliance with the present plan. Herein, "small particle Soups" are any of the Soups described in this subsection ("Solid food particles: Small Particle Soups")

The optional solid food particles can be any macroscopic food particles in the Soup, i.e. particles that can be distinguished with the naked eye. The solid food particles can comprise a meat component and/or a vegetable component. The solid food components optionally comprise one or more additional components, including any of grains, pasta, vitamins, anti-dementia agents, anti-oxidants, fiber, odiferous components, carbohydrates, fats, and proteins, e.g. those taught herein.

Optionally, the solid food particles are vegetable components or meat components. Small vegetable solid food particles can be provided in any manner. For example, the food particles can include grains (e.g. rice or corn), pieces of vegetables (e.g. vegetable chunks larger than corn-size), or pieces of meat (e.g. chunks of meat).

The Soup can be formulated with a small food particle size in any manner.

Optionally, the Soup comprises less than 20 solid food particles having a volume greater than about 20 $cm^3$. For example, the Soup can comprise less than 10 (e.g. less than 5) solid food particles having a volume greater than about 20 $cm^3$ or no solid food particles having a volume greater than about 20 $cm^3$. Optionally, the Soup comprises less than 20 solid food particles having a volume greater than about 10 $cm^3$.

Optionally, less than 50% of the total solid particle food volume is provided by solid food particles having a volume greater than about 20 $cm^3$. Optionally, less than 80% (e.g. less than 60%) of the total solid particle food volume is provided by solid food particles having a volume of less than about 0.2 $cm^3$.

Optionally, at least 50% of the total solid food particle volume other than pasta and grain is provided by solid food particles having a volume about 0.2 $cm^3$ to about 15 $cm^3$.

Optionally, the Soup comprises a maximum solid food particle size of about 20 $cm^3$ or less. For example, the maximum sold food particle size can be less than any of: about 15 $cm^3$, about 10 $cm^3$, about 5 $cm^3$, about 3 $cm^3$, or about 2 $cm^3$.

Optionally, the Soup comprises a maximum solid food particle length about 5 cm or less. For example, the maximum sold food particle length can be less than any of: 4 cm, 3 cm, 2 cm, or 1.4 cm.

Optionally, the Soup comprises solid food particles with a $D_{90}$ of 5 cm or less. For example, the $D_{90}$ can be any of: 4 cm or less, 3 cm or less, 2 cm or less, or 1 cm or less. Optionally, said solid food particles with a $D_{90}$ are solid food particles with a length greater than 0.5 mm. Optionally, said solid food particles with a $D_{90}$ are meat particles. Optionally, said solid food particles with a $D_{90}$ are vegetable particles. Optionally, said solid food particles with a $D_{90}$ are solid food particles other than grains.

In one embodiment, the Soup comprises solid food particles with a $V_{90}$ of 20 $cm^3$ or less. For example, the $V_{90}$ can be less than any of: about 15 $cm^3$, about 10 $cm^3$, about 5 $cm^3$, about 3 $cm^3$, about 2 $cm^3$, or about 1 $cm^3$. Optionally, said solid food particles with a $V_{90}$ are solid food particles with a volume than 0.5 $cm^3$. Optionally, said solid food particles with a $V_{90}$ are meat particles. Optionally, said solid food particles with a $V_{90}$ are vegetable particles. Optionally, said solid food particles with a $V_{90}$ are solid food particles other than grains.

Optionally, the Soup comprises mashable food particles and/or non-mashable food particles. Mashable food particles are any food particles that can be mechanically disrupted to the point of swallowing by squeezing the food particle between the tongue and palate. For example, starchy foods such as potatoes can be made mashable with sufficient boiling.

Optionally, the Soup comprises non-mashable solid food particles exhibiting one or more of the following properties: a maximum solid food particle size of 20 cm$^3$, a maximum solid food particle length of less than about 5 cm, a $D_{90}$ of 5 cm or less, and a $V_{90}$ of 20 cm$^3$ or less. Optionally, said solid food particles are meat particles, vegetable particles, or solid food particles other than grains.

Water and Soup Volume

A Soup, according to the present invention, comprises more than about 30% water, optionally about more than 40% or 50% or 60% or 70% or 80% or 90% water (w/w). In addition to facilitating consumption, the water component, at volumes taught herein, are useful in preventing or treating dehydration, a typical feature of dementia. Surprisingly, the nutritional plan of the present invention, when combined with the resultant compliance, can effective maintain hydration.

Optionally, the Soup comprises 190 ml to 2500 ml of water, e.g. between about 300 ml and about 710 ml. Through insight of the inventor, surprisingly, this optional serving size is a "sweet spot" that provides the highest subject compliance, while also meeting the nutritional needs when consumed.

It has been discovered that the serving size of the present invention, especially when combined with the other features of the invention, can have a remarkable impact on subject compliance, which results in positive medical impact. For reasons not completely understood, when serving size is excessive, dementia subjects may become averse to eating. Too small of serving sizes can result in hypo-nutrition or lack of recognition of the food and under consumption.

The amount of water in a Soup can be determined by quantifying the water weight of the Soup, where the water weight of the Soup in mg is equal to the water volume of the Soup in ml (1 ml water=1 mg).

A Soup of the present invention can be provided as a ready-to-eat Soup. A ready-to-eat Soup is formulated with a volume of water such that no additional water needs to be added prior to consumption.

The total volume of a Soup is 200 to 2000 ml. The total volume of a soup can be determined by formulating the soup with the selected ingredients, allowing the soup to equilibrate at room temperature (i.e. to allow any absorbent food particles to absorb water, oil, or other liquids) and measuring the volume.

Fats

In the present Soup, about 20% to about 80% of the total calories are provided by fat.

Optionally, at least about 30% (e.g. to about 30% to about 65%) of the total calories are provided by fat (herein, a "high fat" Soup). Alternatively, less than about 30% of the total calories are provided by fat (herein, a "low fat" Soup).

A Soup of the invention can contain fat from any source. Useful sources of fat include, e.g. extracted or non-extracted fats from meats or vegetables. For example, the fat in the Soup can include fat from any of butter fat from cream and other dairy sources, animal fat such as chicken fat or lard, vegetable oil, vegetable shortening, and other vegetable fats such as cocoa butter, illipe, shea, palm, palm kernal, sal, soybean, cottonseed, coconut, rapeseed, canola, and sunflower oils.

Essential polyunsaturated fatty acids: Omega-3 and Omega 6 fatty acids

Optionally, the fats in a Soup of the present invention also contain essential polyunsaturated fatty acids of the omega-3 acid type. In one embodiment, omega-3 fatty acids are present in an amount of at least about 100 mg (e.g. 200 mg to about to 2 g). Food substances that are rich in omega 3 fatty acids and optionally included in the present Soup are the fishes halibut, mackerel, salmon, trout and tuna and nutritional plants sources perilla, chia seed, flax, and camelina. Additionally, or alternatively, the omega-3 fatty acids are provided as a supplement, e.g. as a fish or algal extract.

Optionally, the Soup comprises one or more Omega-3 fatty acids selected from eicosapentaenoic acid ('EPA') and docosahexaenoic acid ('DHA'). Optionally, the Soup comprises at least 300 mg DHA (e.g. at least 500 mg, or about 500 mg to about 3000 mg).

Optionally, the ratio of omega-3 fatty acids to omega 6 fatty acids is at least 1 to 3 or optionally at least 1 to 1, or optionally at least 2 to 1, or optionally at least 3 to 1, or optionally at least 4 to 1.

It is interesting to note that DHA in mice bred to develop the plaques and brain tangles associated with Alzheimer's disease causes a markedly lower levels of beta-amyloid and tau proteins than those in the control group (Green, K. Journal of Neuroscience, Apr. 18, 2007; vol 27. News release, University of California, Irvine.). Without being bound my theory, the inventor believes that the unexpected therapeutic efficacy of Soups taught herein can be linked, in part, to the negative effect of dietary omega 3 fatty acids on plaque production in dementia patients.

Medium Chain Triglycerides ("MTCs")

Optionally, a substantial portion of the fat comprises medium chain triglycerides (i.e. C6 to C12), e.g. about 2% to about 40% of the calories are provided by MCT. Optionally, MTCs are provided in an amount that enhances ketone body formation or induces a state of ketosis upon consumption of the Soup. Optionally, at least about 10% to about 50% of the fat calories are provided by medium chain triglycerides (a "high medium chain triglycerides" Soup). Optionally, the ratio (w/w) of medium chain triglycerides to long chain triglycerides ('LCTs') is greater than 1:1 (e.g. at least 3:2, at least 2:1, or at least 3:1). Optionally, the Soup comprises at least about 10 g of medium chain triglyceride (e.g. 10 g to 50 g, 15 g to 50 g, or 20 to 40 g). Sources of medium chain triglycerides include coconut oil (e.g. virgin or extra virgin coconut oil), olive oil, milk fat, butter, palm oil, medium chain triglyceride oil, and glycerol trioctanoate. Optionally, MCT provided about 2% to 40% of total calories in a high MTC Soup; optionally about 10% to about 40%.

Exemplary sources of MTCs are coconut oil, palm kernel oil, and purified preparations.

Without being bound by theory, through insight of the inventor, MTCs, known to be ketogenic, are especially useful in the diet of dementia subjects because ketones, which can cross the blood-brain barrier, serve as an alternate (to glucose) energy source in the brain and may provide improved cognitive function. Moreover, an increase in metabolic efficiency (Peterman MG. The ketogenic diet in the treatment of epilepsy: a preliminary report. Am J Dis Child. 1924; 28(1):28-33) can retard or prevent weight loss (or result in weight gain) when introduced in the in the diet of dementia subjects.

Protein

In the present Soup, about 10% to about 45% of the total calories are provided by protein. Optionally, less than about 25% of the total calories (e.g. 10% to about 25%) are provided by protein (a "low protein" Soup).

The protein in the Soup can be from any source. Useful sources of protein include, e.g. extracted or non-extracted protein from meats and/or vegetables. For example, protein in the Soup is optionally from any of a dairy protein source (e.g. whole milk, skim milk, condensed milk, evaporated milk, whey, casein non-fat milk solids). Useful non-extracted sources of protein include, e.g. solid food particles (e.g. meat or vegetable particles). Useful sources of extracted protein include, e.g. whey, casein, soy protein, egg protein, pea protein, hemp protein, and rice protein.

Through insight of the inventor, it has been discovered that low protein Soups of the invention can be consumed by dementia subjects to reduce dementia symptoms. For example, low protein Soups can be self administered as part of nutritional plan that calls for periodic or cyclic protein restriction. Without limiting the scope of the invention, the Applicant believes that such low protein (or alternating protein) levels in the present Soups reduce tau phosphorylation and circulating levels of IGF-1, changes that are associated with protection against age-related neuropathologies and improve behavioral performance in dementia subjects.

Carbohydrate

In the present Soup, about 10% to about 65% of the total calories are provided by carbohydrate. Optionally, about 10% to about 50% of the total calories are provided by carbohydrate (a "low carbohydrate" Soup). Optionally, less than 10% of the total calories are provided by simple carbohydrates (a "low sugar" Soup). Optionally, less than 5% of the total calories are provided by refined sugars (a "low refined sugar" Soup). According to the present invention, insoluble fiber is not included in the calculation of amount of carbohydrates or carbohydrate caloric distribution.

Optionally, less than 50% w/w (e.g. less than 20%) of the carbohydrates are simple carbohydrates. Optionally, at least 70% w/w of the carbohydrates are complex carbohydrates or soluble fiber.

Useful sources of carbohydrates include starchy vegetables such as grains (e.g. whole grain), non-starchy vegetables, vegetables, and beans. Other examples of useful carbohydrate sources include rice, barley, wheat, oats, tubers, potatoes, legumes, nuts, and seeds. Other sources of carbohydrates are well-known in the art.

Through insight of the inventor, it has been discovered that low carbohydrate, low sugar, and/or low refined sugar Soups of the invention can be consumed by dementia subjects to provide one or more positive effects. For example, without being bound by theory, it is believed that such Soups can be consumed to regulate insulin resistance and toxic ceremides that contribute to neurodegeneration. Additionally, it is believed that such low carbohydrate and/or low refined sugar Soups can be consumed (optionally as a low protein and/or high medium chain triglycerides Soup) to induce ketosis, a state of elevated ketone body-based metabolism, which provides the brain an alternative energy source to glucose. Without being bound by theory, it is believed that such an alternative energy source is beneficial, especially for a dementia patient who already exhibits insulin resistance.

Fiber

A Soup of the present invention comprises dietary fiber. Optionally, the Soup comprises soluble fiber and insoluble fiber. Optionally, the Soup comprises fiber in an amount of at least about 10 grams of fiber per 1000 calories (a "high fiber" Soup). Optionally, the Soup comprises fiber in an amount of at least about 0.25 grams to about 30 gm.

Useful fibers include, e.g. cellulose, gum arabic, gum acacia, and fructose oligosaccharides such as inulin. Exemplary sources of fiber include grains (e.g. oats, barley, corn, and wheat, or bran), vegetables (e.g. chard, collards, kale, mustard greems, spinach, artichokes, brussel sprouts, broccoli, lima beans, mushrooms, okra, parsnips, peas, plantain, potatoes with peels, pumpkin, sauerkraut, sweet potatoes, or turnip), fruits, and beans (e.g. chickpeas, lentils, split peas, soybeans, blackeyed peas, baked beans, fava beans, kidney beans, or pinto beans).

Antioxidants

Soups of the present invention comprise substantial levels of antioxidants. It has been discovered here that the challenge of delivering antioxidants to dementia subjects can be met by Soups of the invention. Surprisingly, dementia subjects willingly ingest antioxidants when provided in a present Soup, e.g. as component of a food substance such as vegetables or as a supplement. Optionally, the present Soup contains effective amounts of one or more of the antioxidants selected from: vitamin A, beta-carotene, vitamin C, Vitamin E, cysteine, glutathione, lipoic acid, anthocyanidins, co-enzyme Q10, selenium, and melatonin. Food substances in the present invention can include dark-skinned vegetables such as kale, cabbage (especially red), spinach, brussel sprouts, alfalfa sprouts, broccoli, beets, red bell pepper, sweet pepper, onion, red beans, wheat bran, corn and eggplant.

The Soup of the present invention can provide a substantial portion of antioxidants. The total amount of antioxidants in a given quantity of Soup can be measured by any means, for example, by the ORAC (Oxygen radical absorbance capacity) method, by Folin-Ciocalteu reagent, or by the Trolox equivalent antioxidant capacity assay. In one embodiment, a Soup contains at least about 1,000 or at least about 2,000 or at least about 5,000 ORAC units (a "high antioxidant" Soup). A high antioxidant Soup can also be defined by its antioxidant levels as quantified by free radical-scavenging activity ("FRSA") according to Re, R., Pellegrini, N., Proteggente, A., Pannala, A., Yang, M. & Rice-Evans, C. (1999) Antioxidant activity applying an improved ABTS radical cation decolorization assay. Free Radic. Biol. Med. 26: 1231-1237, where antioxidant can be reported as Vitamin C mg equivalents (i.e. free radical scavenging activity in comparison to mg of Vitamin C). A high antioxidant Soup contains at least about 100 mg (e.g. about 100 mg to about 500 mg) Vitamin C equivalent by FRSA.

Anti-dementia Agents

While underlying mechanisms are poorly understood, there is growing evidence that certain components, when digested, can have a positive effect of dementia. Optionally, the present Soup further comprises one or more of anti-dementia agents commonly believed to be beneficial such as *Ginkgo Biloba*, turmeric, Astaxanthin, and medium chain triglycerides (e.g. coconut oil or triglyceride oil containing caprylic acid and/or capric acid). Accordingly, a Soup of the invention can optionally be provided with an effective amount of an anti-dementia agent that reduces one or more symptoms of dementia.

Odiferous Components

Through insight of the inventor, it has been discovered that providing odiferous components to the present Soup can have a remarkable positive impact on subject compliance. Without limiting the scope of the invention, the inventor believes that prior memories (e.g. in childhood) of a smell (or odor) associated with food and eating, especially when combined with a recognizable visual image (e.g. soup), can stimulate appetite and positive emotions, thus markedly increasing subject compliance. This result is even more remarkable when combined with a present container that has appearances of a container that relates to food storage, preparation, or eating (e.g. a canning jar, a cooking pot, or a soup bowl).

While the odiferous components of the present invention can be any odiferous components, examples are esters that are released from onions, garlic, herbs, beef, chicken, and pork, especially when optionally heated.

Vitamins and Elements

Certain vitamins are believed to beneficial to dementia subjects. Through insight of the inventor, certain vitamins are optionally included in the Soup. These vitamins, when combined with the other constituents, improve one or more of nutritional status, subject compliance, QoL, or caregiver load.

Vitamins can be provided in the Soup in any manner. For example, the Soup can be formulated with food components that contain the vitamin(s) and/or the Soup can be supplemented with vitamins (e.g. synthetic or extracted vitamins). In one embodiment, one or more vitamins are provided by food components, wherein the vitamin exhibits a sustained release after consumption of the Soup in comparison to a vitamin supplement.

Of the optional vitamins useful according to the present invention are vitamin D, vitamin B12, folate, beta-carotene, and vitamin E and C (alone or in combination).

Optionally the Soup comprises folate in an amount of at least 200 µg (e.g. about 400 µg to about 1500 mg).

Optionally the Soup comprises vitamin B6 in an amount of at least about 10 mg (e.g. about 10 mg to about 100 mg), for example, as pyridoxine HCl.

Optionally the Soup comprises vitamin B12 in an amount of at least about 100 µg (e.g. about 300 µg to about 2000 µg), for example, as cyanocobalamin.

Optionally the Soup comprises vitamin B12 in an amount selected from about 200 µg to about 1000 µg.

Optionally the Soup comprises vitamin E in an amount of at least about 100 IU, e.g. at least about 200 IU.

Optionally, the Soup comprises vitamin C in an amount of at least about 120 mg (e.g. as ascorbic acid). For example, the Soup can comprise at least about 300 mg of vitamin C.

Optionally the Soup comprises beta-carotene in an amount of at least about 10,000 IU.

Optionally, the Soup comprises zinc in an amount of at least about 20 mg.

Optionally, the Soup provides a substantial portion of the DNN (e.g. RDA or IA) for the subject or a particular group of subjects; for example, any of about at least 30% or 40% or 50% or 60% or 70% or 80% or 90% or 100% of one or any combination of vitamin A, vitamin C, vitamin D, vitamin E, vitamin K, thiamin, riboflavin, niacin, vitamin $B_6$, Folate, vitamin $B_{12}$, pantothenic, biotin, and choline.

Optionally, the Soup meets about 50% or about 80% or about 100% of the DNN (e.g. RDA or IA) for one or more (e.g. all) of the elements selected from: Calcium, Chromium, Copper, Fluoride, Iodine, Iron, Magnesium, Manganese, Molybdenum, Phosphorus, Selenium, Zinc, Potassium, Sodium, and Chloride.

In one embodiment, the DNN is the RDA or IA for subjects (e.g. females or males) over 70 years of age, as set by the Institute of Medicine of the U.S. National Academy of Sciences. (Dietary Reference Intakes (DRIs): Recommended Intakes for Individuals, Food and Nutrition Board, Institute of Medicine, National Academies, 2004. Available from the URL: <http://www.iom.edu/Global/News%20Announcements/~/media/Files/Activity%20Files/Nutrition/DRIs/DRI_Summary_Listind.pdf>. Retrieved 12 Jun. 2013).

Vegetable Component

A Soup of the invention optionally comprises solid food particles comprising a vegetable component. The vegetable component can be provided as solid food particles and/or as part of a liquid phase of the Soup.

Optionally, the Soup comprises a starchy vegetable, a non-starchy vegetable, or both.

Optionally, the Soup comprises one or more vegetable components selected from allium vegetables, cruciferous vegetables, brassica vegetables, composite vegetables, goosefoot/amaranth vegetables, gourds, grass vegetables, legumes, umbelliferous vegetables, and peppers.

Optionally, the Soup comprises one or more vegetable components selected from leafs, pod vegetables, seed, roots, tubers, flower vegetables, bud vegetables, and fruit vegetables.

Optionally, the Soup comprises a vegetable other than at least one vegetable selected from allium vegetables, cruciferous vegetables, brassica vegetables, composite vegetables, goosefoot/amaranth vegetables, gourds, grass vegetables, legumes, umbelliferous vegetables, and peppers.

Optionally, the Soup comprises a vegetable other than at least one vegetable selected from leafs, pod vegetables, seed, roots, tubers, flower vegetables, bud vegetables, and fruit vegetables.

Many vegetables provide a good source of vitamins and both digestible carbohydrates and fiber while others provide a good source of other micro and macro nutrients. In addition, vegetables are taught herein that have well-characterize nutrient profiles. Accordingly, with the teachings provided herein, the skilled artisan can readily select vegetables to provide Soups of the invention, including Soups with tailored levels of antioxidants, vitamins, and macromolecule distributions.

Optionally, the Soup comprises a starchy vegetable. Optionally, the starchy vegetable is provided as solid particles. Examples of useful starchy vegetables include starchy roots or tubers such as potatoes, yams, cassava, sweet potato, and grains such as oats, corn, and rice.

Optionally, the Soup comprises a non-starchy vegetable. Optionally, the non-starchy vegetable is provided as solid particles. Examples of useful non-starchy vegetables include alfalfa sprouts, amaranth, artichoke, asparagus, avocado, bamboo shoots, beans (e.g. green, italian, yellow or wax), bean sprouts, beets, broccoli, bok choy, bamboo shoots, brussels sprouts, cabbage, carrots, cauliflower, celery, chicory, chinese cabbage, chinese spinach, cucumber, eggplant, fennel, green onions, greens (e.g. beet greens, collard, dandelion, kale, mustard, turnip), hearts of palm, herbs (e.g. parsley, cilantro, basil, rosemary, thyme), jicama, kohlrabi, leeks, lettuce (endive, escarole, romaine or iceberg), mushrooms, okra, onions, parsley, peppers (green, red, yellow, orange, jalapeno), radishes, rhubarb, rutabaga, sauerkraut, scallions, snow peas or pea pods, spinach, summer squash, swiss chard, tomato, turnips, water chestnuts, watercress, and zucchini.

Optionally, the Soup comprises an allium vegetable. Examples of useful allium vegetables include chives, garlic, leeks, onion, and shallot.

Optionally, the Soup comprises a brassica vegetable. Examples of useful brassica vegetables include bok choy, broccoli, brussels sprouts, cabbage, cauliflower, chinese cabbage (napa cabbage), collard greens, kohlrabi, mustard greens, rapeseed oil (canola), rapini, rutabaga, and turnip.

Optionally, the Soup comprises a cruciferous vegetable. Examples of useful cruciferous vegetables include the brassica vegetables and arugula (rocket), daikon radish, horseradish, maca, radish, virginia pepperweed, wasabi, and watercress, Optionally, the Soup comprises a composite vegetable. Examples of useful composite vegetables include artichoke, chamomile, chicory, dandelion, endive, Jerusalem artichoke, lettuce, romaine, safflower, salsify, and sunflower.

Optionally, the Soup comprises a goosefoot/amaranth vegetable. Examples of useful goosefoot/amaranth vegetables include amaranth, beet, chard, lamb's-quarters, quinoa, spinach, and sugar beet.

Optionally, the Soup comprises a gourd. Examples of useful gourds include cantaloupe, cucumber, melons, pumpkin, squash, watermelon, and zucchini.

Optionally, the Soup comprises a grass vegetable. Examples of useful grass vegetables include bamboo shoots, sweet corn, and wheatgrass.

Optionally, the Soup comprises a legume. Examples of useful legumes include alfalfa, beans, carob, chickpea, green beans, jicama, lentil, pea, peanut, and soy.

Optionally, the Soup comprises an umbelliferous vegetable. Examples of useful umbelliferous vegetables include caraway, carrot, celery, cilantro, cumin, dill, fennel, parsley, and parsnip.

Optionally, the Soup comprises leaves. Examples of useful leaves include spinach, sorrel, chard, lettuce, and cabbage.

Optionally, the Soup comprises pod vegetables. Examples of useful pod vegetables include green beans, wax beans, runner beans, and mange-tout peas.

Optionally, the Soup comprises seeds. Examples of useful seeds include lentils and flageolet beans.

Optionally, the Soup comprises root vegetables. Examples of useful root vegetables include carrots, beets, turnips, and radishes.

Optionally, the Soup comprises tubers. Examples of useful tubers include potatoes, sweet potatoes, cassava, and yams.

Optionally, the Soup comprises flower vegetables or bud vegetables. Examples of useful flower and bud vegetables include cauliflower, artichokes, asparagus, and broccoli.

Optionally, the Soup comprises fruit vegetables. Examples of useful fruit vegetables include courgette, zucchini, aubergine, eggplant, and tomato.

Meat Component

A Soup of the invention optionally comprises a meat component. The meat component can be provided as solid food particles and/or as part of a liquid phase of the Soup.

Optionally, the Soup comprises a meat component selected from beef, sheep (e.g. lamb), pork, poultry, fish, shellfish, venison, ostrich, elk, emu, and bison.

Optionally, the Soup comprises white meat or dark meat.

Optionally, the Soup comprises fatty meat or lean meat.

Many meats provide a good source of protein. Meats can also provide a source of fat, vitamins, and other micro and macro nutrients. In addition, meats are taught herein that have well-characterize nutrient profiles. Accordingly, with the teachings provided herein, the skilled artisan can readily select meats to provide Soups of the invention, including Soups with tailored levels of antioxidants, vitamins, and macromolecule distributions.

Calorie Content.

The present Soup is rich in calories, e.g. comprising about 0.25 to about 10 calories per ml, optionally about 0.25 to about 5 calories per ml; optionally about 0.5 to about 2 calories per ml.

Optionally, the Soup comprises about 300 to about 3500 calories, e.g. about 300 to about 2500 calories, about 500 to about 2000 calories, or about 400 to about 1200 calories.

According to the present invention, the term "calorie" or "cal" is used to refer to food calories. The number of calories in a Soup can be calculated as the sum of the number calories provided by each of the macronutrients. The number of calories provided by each of the macronutrients can be calculated by quantifying the amount of macronutrient and multiplying the amount of macronutrient by the respective macronutrient calorie factor, i.e. 9 calories/gram fat, 4 calories/gram protein, and 4 calories/gram carbohydrate (not including insoluble fiber), as is well-known in the art.

Viscosity

Optionally, the Soup comprises a liquid phase having a viscosity (at 30° C.) less than 500 times that of water. Optionally, the liquid phase has a viscosity of less than any of 200 times that of water, 150 times that of water, 100 times that of water, 60 times that of water, 40 times that of water, 20 times that of water, 10 times that of water, 5 times that of water, or 2 times that of water.

The viscosity of olive oil is about 100 times that of water at room temperature. Accordingly, such low-viscosity Soups can be readily consumed without the addition of water. Without being bound by theory, it is believed that enhanced patient compliance can be due, at least in part, to the provision of such ready-to-eat Soups.

The viscosity of the Soup can be manipulated, e.g. by partitioning any swellable or bulking food components to a solid food particle rather than the liquid phase. For example, noodles or vegetables high in swellable or bulking food components such as soluble fiber and starch can be selected as solid food particles in order to partition these viscosity-increasing components away from the liquid phase.

The viscosity of a soup with solid food particles can be measured, e.g. after passing the soup through a screen (e.g. a #14 mesh screen with a 1410 micron mesh size) to remove solid food particles.

Bread

As detailed above, the Soups can elicit recognition (and compliance) from dementia subjects. Unexpectedly, subjects when also offered a bread product (e.g. a muffin, biscuit, bread, toast, etc.), can have an even greater compliance with the nutritional program—i.e. the subjects will not only more consistently consume the Soup, but they can get the added benefit of the calories and fiber of the bread product.

Containers

The products of the present invention can be packaged in any container but are especially useful when packaged in a reversibly closed (i.e. closed container that can be opened) in an easy-open and/or microwavable container. Additionally, containers are especially useful according to the present invention that have a strong sense of familiarity to the subjects; e.g, containers that resemble a soup bowl, a traditional canning jar, a cooking pot, or have a drawing or photograph of such soup bowl, etc.

Optionally, the container is a bowl, wherein the bowl has a width that is greater its height (i.e. the bowl is wider than it is deep). Optionally, the bowl is has a circular cross section. Optionally, the base of the bowl is wider than the mouth of the bowl. Optionally, the bowl is hemispherical, rounded, or has a curved sidewall.

Optionally, the container is a cup, wherein the cup (a defined herein) has a height that is greater its width (i.e. the bowl is deeper than it is wide). Optionally, the cup is has a circular cross section (e.g. a cylindrical cup).

Optionally, the cup or the bowl has a handle to aid in picking the container up.

The container is a sealed container. The sealed container can be, e.g., any container that provides a barrier that completely covers the Soup and prevents or greatly retards the escape of water and food (e.g. without leaking through any container wall).

Optionally, the container is a re-sealable container. Optionally, the re-sealable container comprises a screwable lid, a press-fit lid, an adhesive lid, a vacuum sealable lid (e.g. with suction cup lid or vacuum pump button), a lid having a clip that engages the soup-containing portion of the container, a top having an aperture covered by a slidable lid, or a magnetic lid. Guidance for providing re-sealable containers can be found, e.g. in US20030015542, U.S. Pat. Nos. 8,083,089, 5,269,430, 6,299,033, 8,276,776, 6,626,314, and 8,336,726.

Microwaveable

Microwave ovens offer the general public several convenience features, are easy to operate, and are generally familiar. It has been further discovered here that the present Soups, containers, and nutritional plans are especially effective when combined with a microwave (e.g. microwavable container, microwavable Soups, and nutritional plans that provide microwave instructions). For example, modern microwaves can be provided with pre-configured or automated cooking programs that are activated with the push of a single button (e.g. a "soup" button) or two or a few buttons (e.g. "quick minute" and "start"). Dementia subjects surprisingly have familiarity with these functions, and can learn to follow these very few operational steps and such steps are reinforced by the present container (e.g. a container that looks like a soup bowl or tureen) and by the present Soups (e.g. that have a familiar appearance to soups in encountered and eaten in the subject's past). Without limiting the scope of the invention, the inventor believes that the success of the present invention results from the unexpected force of combining several reinforcing signals that result in improved subject compliance, better nutrition, and less cooking accidents and food burns (and burnt food)

Specially designed packages or cartons for cooking, browning and/or crisping foods in microwave ovens have been known for quite some time. Often, these packages utilize susceptors, or microwave interactive materials which convert microwave energy to heat, to achieve proper or sufficient cooking of the foods contained in the packages. By way of example, U.S. Pat. No. 4,267,420 to Brastad and U.S. Pat. No. 4,641,005 to Seiferth describe the use of various metallized polyester films or susceptors in connection with cooking foods in microwave ovens.

The use of reflective or electrically conductive materials which selectively transmit, absorb and/or reflect microwave energy have also been used in microwave packaging to affect their cooking performance. For instance, U.S. Pat. No. 4,567,341 to Brown describes a vented, microwave pizza carton having a reflective material for shielding portions of the pizza from microwave energy to prevent overcooking.

Multi-functional Containers

The containers of the present invention are optionally multi-functional containers. For example, they can be made of a material that is suitable for heating in the microwave or placed on the stove. Optionally, the container is also suitable for using as a serving container (e.g. an opening that is at least about 80% of the width of the container.

Easy Opening

Optionally, the container is an "easy open" container, e.g., to result in especially high compliance. An easy opening can be achieved in the invention with any easy open features such as a larger pull tab to allow more surface area for gripping, a specialized pop top that does not require the same level of strength or fine motor control, easy open seal, etc. For example, useful containers are taught in EP 1398278, EP 0462767, WO 2006110685, EP 0227736, U.S. Pat. Nos. 8,360,262, 8,063,345, 3,773,207, 3,984,025, 4,555,043, 4,520,943, 4,930,656. Optionally, the container is an easy-open container and is also re-sealable (e.g. a resealable tear-away lid).

Labeling

It has been discovered that additional efficacy (e.g. compliance and nutrition) is achieved when the container comprises a recognizable soup with a recognizable name in easy-to-read print and a standard font. For example, the Soup name can be any common or generic name (traditional or regional name as described in the text referring to Table 1). The name is in a large font, for example, greater than about any of 14 pt, 18 pt, 24 pt, or 36 pt. Recognition and compliance is substantially increased when the label also contains a graphic (or picture) representation of the Soup.

Extended Stability

The Soup of the present invention is contained in a container in a manner that provides for extended stability and provides a means for extending stability. Such extended stability can results from freezing, canning (i.e. method of preserving food in which the food contents are processed and sealed in an airtight container), and/or preservatives. Exemplary preservatives are preservative concentrations of monosodium glutamate, potassium sorbate, sodium phosphate, lactic acid., or sodium chloride.

Container Embodiments

Among the containers that are useful in the present invention are easy open containers, microwaveable containers, re-sealable containers, containers that contain large print (e.g. 10 to 30 font text and/or large pictures of food products), microwavable easy-open containers, large print microwavable easy-open containers, large print microwavable easy-open, re-sealable containers, Optionally, the container has one or more features similar to a soup bowl, e.g. (i) container height is less than the container width; (ii) the opening of the container is at least as wide as the base; (iii) the container comprises a handle.

Optionally, the container has a level of transparency that allows recognition of the Soup through the container.

Optionally, the container has features similar to a canning jar reminiscent of a homemade and home canned soup. Such features include one or more of (1) clear/transparent glass (optionally colored); (2) height greater than the width; (3) a screw lid (optionally functional or reversibly removable); and (4) sized between 250 and 1000 mls. Such containers can be combined with methods that further comprise pouring the soup into a bowl familiar to the subject (by shape or design), further reinforcing subject recognition Optionally, the container is metered to indicate volume of the Soup. Optionally, the inside of the bottom of the container comprises a graphic representation (i.e. and image) or words.

Recognition of Soup

Soups of the present invention optionally comprise food substances that are prepared to preserve recognition on sight by dementia subjects. For example, for vegetal food substances, whole units (or substantial parts thereof) are useful. Examples of recognizable vegetable food substances are a whole kernel of corn, carrots cut into slices laterally or substantial portions of baby carrots, whole tips of broccoli, partial spinach leaves, whole units of pasta (e.g. elbow macaroni), etc. For meat food substances, it has been observed that cubes are more recognizable than shreds of meat.

In order to further stimulate the "recognition-appetite stimulation axis", Soups of the present invention optionally have an appearance of traditional soups such as those of Table 1. These Soups are typically referred to by the key ingredients. For example, S-101 is typically referred to as chicken noodle soup (when the pasta is a type of noodle). S-109 is typically referred to as chicken and rice soup. The skilled artisan will immediately recognize that in different cultures, nationalities, or regions, the common names for these soups may differ. In the present invention, typical names for these soups are used for a label on the container and the food substances are cut for maximum recognition by the subject (discussed elsewhere here).

TABLE 1

| Soup | Meat | Non-starchy vegetable | Starch | tomato |
|---|---|---|---|---|
| S-100 | none | | pasta | none |
| S-101 | Chicken | | pasta | none |
| S-102 | Pork | | pasta | none |
| S-103 | Turkey | | pasta | none |
| S-104 | Beef | | pasta | none |
| S-105 | Fish | | pasta | none |
| S-106 | Lamb | | pasta | none |
| S-107 | Goat | | pasta | none |
| S-108 | none | | rice | none |
| S-109 | Chicken | | rice | none |
| S-110 | Pork | | rice | none |
| S-111 | Turkey | | rice | none |
| S-112 | Beef | | rice | none |
| S-113 | Fish | | rice | none |
| S-114 | Lamb | | rice | none |
| S-115 | Goat | | rice | none |
| S-116 | none | | potato | none |
| S-117 | Chicken | | potato | none |
| S-118 | Pork | | potato | none |
| S-119 | Turkey | | potato | none |
| S-120 | Beef | | potato | none |
| S-121 | Fish | | potato | none |
| S-122 | Lamb | | potato | none |
| S-123 | Goat | | potato | none |
| S-124 | none | yes | pasta | none |
| S-125 | Chicken | yes | pasta | none |
| S-126 | Pork | yes | pasta | none |
| S-127 | Turkey | yes | pasta | none |
| S-128 | Beef | yes | pasta | none |
| S-129 | Fish | yes | pasta | none |
| S-130 | Lamb | yes | pasta | none |
| S-131 | Goat | yes | pasta | none |
| S-132 | none | yes | rice | none |
| S-133 | Chicken | yes | rice | none |
| S-134 | Pork | yes | rice | none |
| S-135 | Turkey | yes | rice | none |
| S-136 | Beef | yes | rice | none |
| S-137 | Fish | yes | rice | none |
| S-138 | Lamb | yes | rice | none |
| S-139 | Goat | yes | rice | none |
| S-140 | none | yes | potato | none |
| S-141 | Chicken | yes | potato | none |
| S-142 | Pork | yes | potato | none |
| S-143 | Turkey | yes | potato | none |
| S-144 | Beef | yes | potato | none |
| S-145 | Fish | yes | potato | none |
| S-146 | Lamb | yes | potato | none |
| S-147 | Goat | yes | potato | none |
| S-148 | none | | pasta | tomato |

TABLE 1-continued

| Soup | Meat | Non-starchy vegetable | Starch | tomato |
|---|---|---|---|---|
| S-149 | Chicken | | pasta | tomato |
| S-150 | Pork | | pasta | tomato |
| S-151 | Turkey | | pasta | tomato |
| S-152 | Beef | | pasta | tomato |
| S-153 | Fish | | pasta | tomato |
| S-154 | Lamb | | pasta | tomato |
| S-155 | Goat | | pasta | tomato |
| S-156 | None | | rice | tomato |
| S-157 | Chicken | | rice | tomato |
| S-158 | Pork | | rice | tomato |
| S-159 | Turkey | | rice | tomato |
| S-160 | Beef | | rice | tomato |
| S-161 | Fish | | rice | tomato |
| S-162 | Lamb | | rice | tomato |
| S-163 | Goat | | rice | tomato |
| S-164 | None | | potato | tomato |
| S-165 | Chicken | | potato | tomato |
| S-166 | Pork | | potato | tomato |
| S-167 | Turkey | | potato | tomato |
| S-168 | Beef | | potato | tomato |
| S-169 | Fish | | potato | tomato |
| S-170 | Lamb | | potato | tomato |
| S-171 | Goat | | potato | tomato |
| S-172 | None | yes | pasta | tomato |
| S-173 | Chicken | yes | pasta | tomato |
| S-174 | Pork | yes | pasta | tomato |
| S-175 | Turkey | yes | pasta | tomato |
| S-176 | Beef | yes | pasta | tomato |
| S-177 | Fish | yes | pasta | tomato |
| S-178 | Lamb | yes | pasta | tomato |
| S-179 | Goat | yes | pasta | tomato |
| S-180 | none | yes | rice | tomato |
| S-181 | Chicken | yes | rice | tomato |
| S-182 | Pork | yes | rice | tomato |
| S-183 | Turkey | yes | rice | tomato |
| S-184 | Beef | yes | rice | tomato |
| S-185 | Fish | yes | rice | tomato |
| S-186 | Lamb | yes | rice | tomato |
| S-187 | Goat | yes | rice | tomato |
| S-188 | none | yes | potato | tomato |
| S-189 | Chicken | yes | potato | tomato |
| S-190 | Pork | yes | potato | tomato |
| S-191 | Turkey | yes | potato | tomato |
| S-192 | Beef | yes | potato | tomato |
| S-193 | Fish | yes | potato | tomato |
| S-194 | Lamb | yes | potato | tomato |
| S-195 | Goat | yes | potato | tomato |

Formulations

Soups of the present invention are made according to any of Formulation 1 through Formulation 20, and combinations and variations thereof, as set forth in Table 6 and are made in the form of Soups S-100-S195 as set forth in Table 1. Each of the compositions made by manufacturing each of the Formulations in each of the Soup forms are specifically contemplated to address the various needs within the dementia population.

In one embodiment, the Soup is a high-fat Soup.

In one embodiment, the Soup is a low carbohydrate Soup.

In one embodiment, the Soup is a low protein Soup.

In one embodiment, the Soup is a low refined sugar Soup.

In one embodiment, the Soup is a high-fat, low carbohydrate Soup.

In one embodiment, the Soup is a high-fat Soup, low refined sugar Soup.

In one embodiment, the Soup is a low carbohydrate, low protein Soup.

In one embodiment, the Soup is a low protein, low refined sugar Soup.

In one embodiment, the Soup is a high-fat, adequate protein, low carbohydrate Soup.

In one embodiment, the Soup is a high-fat, low protein, low carbohydrate Soup.

In one embodiment, the Soup is a high-fat, low protein, low carbohydrate, low sugar.

The above embodiments, and the other Soups of the present invention, optionally contain odiferous components.

The above embodiments, and the other Soups of the present invention, optionally contain one or more anti-dementia agents.

The above embodiments, and the other Soups of the present invention, optionally contain one or more antioxidants.

In one embodiment, the Soup has a caloric distribution according to Table 2 and optionally, antioxidant in an amount of about 100 to about 500 mg equivalents of vitamin C as calculated by FRSA.

TABLE 2

| Fraction | Calories Per Serving | % of total calories |
|---|---|---|
| Total | 510-601 | |
| Fat | 277-289 | 46-56 |
| MTC | 73-104 | 12-20 |
| Protein | 102-146 | 20-24 |
| Carbohydrates | 111-179 | 21-30 |

In one embodiment, the Soup has a caloric distribution according to Table 3 or within about 10% or about 20% or about 30% or about 40% of the amounts of Table 3 and optionally, antioxidant in an amount of about 100 to about 500 mg equivalents of vitamin C as calculated by FRSA. As used here and in this context, "within about 10% means 90% to 110% for each amount.

TABLE 3

| Fraction | Calories Per Serving | % of total |
|---|---|---|
| Total | 545 | |
| Fat | 283 | 50 |
| MTC | 87 | |
| Protein | 124 | 22.7 |
| Carbohydrates | 138 | 25 |

In one embodiment, the Soup (any embodiments) optionally has a fat composition as set forth in Table 4 and optionally, antioxidant in an amount of about 100 to about 500 mg equivalents of vitamin C as calculated by FRSA.

TABLE 4

| Ingredient | Amount Per Serving | % Daily value |
|---|---|---|
| Total Fat | Amount Per Serving (g) | % Daily value |
| Saturated Fat | 32.1 | 48-50% |
| Monounsaturated Fat | 14.8 | 69-78% |
| Polyunsaturated Fat | 10.9 | |
| Trans Fatty Acids | 3.55 | |

In one embodiment, the Soup has a fat composition as set forth in Table 5 or within about 10% or about 20% or about 30% of the amounts of Table 5 and optionally, antioxidant in an amount of about 100 to about 500 mg equivalents of vitamin C as calculated by FRSA.

TABLE 5

| Ingredient | Amount Per Serving | % Daily value |
|---|---|---|
| Total Fat | 32.1 | 48-50% |
| Saturated Fat | 14.8 | 69-78% |
| Monounsaturated Fat | 10.9 | |
| Polyunsaturated Fat | 3.55 | |
| Trans Fatty Acids | .04 g | |

In one embodiment, the Soup has a caloric distribution according to Table 2, a fat composition as set forth in Table 4, and optionally, antioxidant in an amount of about 100 to about 500 mg equivalents of vitamin C as calculated by FRSA. The Soups in Example 1-Example 3 are species of this embodiment.

In one embodiment, the Soup has a caloric distribution and, a fat composition within about 10% or about 20% or about 30% or about 40% of the average amounts of as set forth in Table 3 and Table 5, and optionally, antioxidant in an amount of about 100 to about 500 mg equivalents of vitamin C as calculated by FRSA. The Soups in Example 1-Example 3 are species of this embodiment.

In one embodiment, the Soup has the composition set forth in one or more of the formulations of Table 6.

TABLE 6

| | Macronutrient caloric distribution | | | Calories | Water | | Anti- | Volume | omega-3 |
|---|---|---|---|---|---|---|---|---|---|
| | protein | fat | carb | (total) | (total) | Vitamins | oxidants | (total) | fatty acids |
| Formulation 1 | ~10%-~45% | ~20%-~65% | ~10%-~65% | ≥1,000 | ~60%-~95% | ≥50% RDA of at least one of D, B12, folate, â-carotene, E, & C | ≥1,000 U ORAC or ≥100 mg equivalents of vitamin C (FRSA). | 200-710 ml | 0.3 g to 3 g |
| Formulation 2 | ~10%-~45% | ~20%-~65% | ~10%-~65% | ≥1,000 | ~60%-~95% | ≥50% RDA of one or more of D, B12, folate, â-carotene, E, & C | | 200-710 mls | 0.3 g to 3 g |

TABLE 6-continued

| | Macronutrient caloric distribution | | | Calories | Water | | Anti- | Volume | omega-3 |
| --- | --- | --- | --- | --- | --- | --- | --- | --- | --- |
| | protein | fat | carb | (total) | (total) | Vitamins | oxidants | (total) | fatty acids |
| Formulation 3 | ~10%-25% | ~30%-65% | ~10%-50% | ≥1,000 | ~~60%-~95% | ≥50% RDA of at least one of D, B12, folate, â-carotene, E, & C | ≥1,000 U ORAC or ≥100 mg equivalents of vitamin C (FRSA) | 200-710 mls | 0.3 g to 3 g |
| Formulation 4 | ~10%-25% | ~30%-65% | ~10%-50% | ≥1,000 | ~~60%-~95% | ≥50% RDA of at least one of D, B12, folate, â-carotene, E, & C | | 200-710 mls | 0.3 g to 3 g |

Nutritional Plan

The Soups, containers, and kits of the present invention can be designed for, inter alia, use with a nutritional plan, e.g., as a method for providing nutrition to dementia subjects. Optionally, the nutritional plan is any regimen (or regimen instructions) for administering one or more Soups of the invention to a dementia patient over a period of time. Optionally, a Soup or kit of the invention comprises instructions which comprise a nutritional plan (e.g. any method or regimen of the invention reduced to writing).

Typically, the instructions contain one or more directives; e.g. any of instructions for:
  a. Opening
  b. Amount to be consumed (e.g. Open one container of food each day and attempt to finish the portion of Soup that is in the container that same day)
  c. Preparation (e.g. There is no need to add anything to the Soup)
  d. Heating (e.g. place in microwave and follow written instructions, or the option of heating on the stove top.
  e. Disposal (e.g. at the end of the day or at the start of the next day), place the lid on the container a place it in a refrigerator or the trash (box, bag, or other designated place).
  f. Marking the container (e.g. Mark the container with the date that it is opened).

By way of example, a nutritional plan according to the present invention, can be also include instructions to take supplements (e.g. vitamins, minerals, fiber, erc), to consume other food substances (e.g. a bread, muffin, roll, or the like).

Kits

Kits of the present invention comprise a plurality of containers, each comprising a present Soup. In one embodiment, the kit contains 5 or 6 or 7 containers (with Soups). In one embodiment, the kit contains about 20, more than about 20, or about 30 containers of Soup. Optionally, the containers of Soups are sub-grouped within the Kit packaging. Any subgrouping known in the art can be used, for example, the kit can contain sleeves, wherein each sleeve contains about 5 or 6 or 7 containers. Optionally, the containers are each numbered consecutively beginning with one or are each labeled with consecutive days of the week to encourage compliance and function as a reminder.

Typically, the kit contains the instructions of a nutritional plan.

Typically, the kit contains a calendar for easier compliance.

Optionally, the kit comprises at least a first Soup and a second Soup, wherein the first Soup is a low-protein Soup and the second Soup is a not a low-protein Soup. Optionally, the second Soup is a high medium chain triglycerides Soup. Optionally, the first Soup is a high medium chain triglycerides Soup.

Optionally, the kit further contains an event monitoring system that collect information concerning when a Soup container was opened. Such systems are well known in the art.

Optionally, event monitoring is provided in the kit as computer readable software or a cellular phone application. Such programs and applications are well known in the art. In one embodiment, the event monitoring system further has a notification function, where the subject is instructed to open a container of Soup by way of a voice, sound, picture, video, etc. Through insight of the inventor, this notification function combined with the kits of the present invention can have a remarkable positive effect on subject compliance with the nutritional plan.

Medical Benefits

Through insight of the inventor, it has been discovered that one or more medical benefits can be achieved through use of a Soup, packaged Soup, kit, or nutritional plan of the present invention. Such benefits may at least include:
  Memory improvement, stabilization, or slow rate of loss
  Reduction in wasting
  Weight gain or weight stabilization
  GI regulation (e.g. bowel regularity)
  Hydration
  Improvement in continence
  Improvement in QoL
  Reduced neurodegeneration
  Increase in longevity

EXAMPLES

Example 1

Country Ham and Bean Soup

The Soup of this Example was prepared from the ingredients set forth in Table 7. The individual ingredients were prepared according to the teaching herein; e.g. with respect to the size of the food particles and the way that they were prepared in order to optimize the "recognition—appetite stimulation" axis.

TABLE 7

| Ingredients: |
| --- |
| 3 cups ham, smoked (½" cubes) |
| 1 medium onion chopped |
| 3 medium carrot, finely chopped |
| 3 medium celery chopped |
| 4 cups kale |
| 6 cups chicken stock or canned chicken broth |
| 2 bay leaves |
| 0.5 tbs cumin |
| 0.5 tbs oregano leaves, 3 crushed |
| 0.5 tbs thyme, crushed |
| 0.5 cup coconut oil |
| 2 tbs chia flour |
| 6 tea bags (12 gm) green tea |
| 1 medium red bell pepper seeded & cut into ¼ inch cubes |
| 1 medium leek, white only, chopped |
| 0.5 tsp pepper |
| 0.5 cup kidney beans |
| 0.5 cup lima beans |
| 0.5 cup lentils, rinsed |
| 0.5 cup chickpeas |
| 0.5 cup great northern beans |
| 0.5 cup pinto beans |
| 0.5 cup navy beans |
| 1 can (15 oz) tomatoes, diced |
| 1 tsp celery seed |
| 4 tbs olive oil |
| 1.5 cup bacon, chopped |
| 1 tsp garlic clove, minced |

Preparation: The Soup was prepared as follows:
1. heat 3 c of stock to boil and fully steep tea bags then remove
2. in the other 3 cups of stock, stir in chia flour. Mix well and set for at least 10 min.
3. saute veggies in oil to tender
4. cook bacon on stove or in oven to crisp (chop fine)
5. combine all ingredients in stock pot or slow cooker—including spices & beans
6. simmer for at least 1 to 2 hrs Cooking Times. The following sets forth the times required for the various steps.
Preparation Time: 1 hour
Cooking Time; 2 hours
Inactive Time: 2 hours
Total Time; 3 hours Nutrition Facts: The nutritional content as set forth in Table 8 and Table 9 was calculated as the sum of each ingredient as obtained from published information. Serving size was calculated as; ⅑ of a recipe (18.2 ounces).

Percent daily values based on the Reference Daily Intake (RDI) for a 2000 calorie diet.

TABLE 8

| Fraction (per serving) | Calories | % of total |
| --- | --- | --- |
| Total | 525 | |
| Fat | 289 | 55 |
| MTC | 104 | 20 |
| Protein | 125 | 24% |
| Carbohydrates | 111 | 21% |
| Alcohol | 0 | 0% |

| Component | Amount per serving | Percent daily values |
| --- | --- | --- |
| Total Fat | 32.7 g | 50 |
| Saturated Fat | 15.6 g | 78 |
| Monounsaturated Fat | 10.9 g | |
| Polyunsaturated Fat | 3.68 g | |
| Trans Fatty Acids | 0 g | |
| Cholesterol | 49 mg | 16 |
| Sodium | 1780 mg | 74 |
| Potassium | 1120 mg | 32 |
| Total Carbohydrates | 28.9 g | 10 |
| Fiber | 8.9 g | 36 |
| Sugar | 4.66 g | |
| Net Carbohydrates | 20.0 g | |
| Protein | 31.47 g | 63 |
| Vitamin A | 9780 IU | 196 |
| Vitamin C | 0.98 mg | 2 |
| Calcium | 42.8 mg | 4 |
| Iron | 148 mg | 821 |
| Vitamin E | 5.11 mg | 51 |
| Vitamin D | 0 IU | 0 |
| Thiamin | 24.8 mg | 1651 |
| Riboflavin | 0.63 mg | 37 |
| Niacin | 0.38 mg | 2 |
| Vitamin B6 | 8.73 mg | 437 |
| Folate | 0.67 µg | <1 |
| Vitamin B12 | 117 µg | 1958 |
| Pantothenic Acid | 0.75 mg | 8 |
| Vitamin K | 1.05 µg | 1 |
| Phosphorus | 512 mg | 51 |
| Magnesium | 417 mg | 104 |
| Zinc | 85.9 mg | 573 |
| Copper | 3.23 mg | 162 |
| Manganese | 0.56 mg | 28 |
| Selenium | 1.09 µg | 2 |
| Alcohol | 0 g | |
| Caffeine | 0 mg | |
| Water | 416 g | |

TABLE 9

| Recipe | Ingredient | Calories | Total Fat | Saturated Fat | Cholesterol | Sodium | Carbohy-drates. |
| --- | --- | --- | --- | --- | --- | --- | --- |
| 3 cups ham, smoked (½" cubes) | 73.27 | 2.57 | 0.86 | 25.67 | 619.27 | 0.00 | 0.00 |
| 1 medium onion chopped | 4.89 | 0.01 | 0.01 | 0.00 | 0.49 | 1.14 | 0.00 |
| 3 medium carrot, finely chopped | 1.13 | 0.01 | 0.00 | 0.00 | 1.88 | 0.27 | 0.00 |

TABLE 9-continued

Ingredient Details

| Recipe | Ingredient | Calories | Total Fat | Saturated Fat | Cholesterol | Sodium | Carbohy-drates. |
|---|---|---|---|---|---|---|---|
| 3 medium celery chopped | 9.00 | 0.08 | 0.02 | 0.00 | 45.50 | 2.00 | 0.00 |
| 4 cups kale | 16.18 | 0.23 | 0.03 | 0.00 | 13.29 | 3.25 | 0.00 |
| 6 cups chicken stock. . . | 25.60 | 0.91 | 0.26 | 0.00 | 489.60 | 0.61 | 0.00 |
| Total | 525.27 | 32.73 | 15.63 | 48.95 | 1776.12 | 28.92 | 0.98 |
| 2 bay leaves | 0.09 | 0.00 | 0.00 | 0.00 | 0.01 | 0.02 | N/D |
| 0.5 tbs cumin | 0.58 | 0.01 | 0.01 | 0.00 | 0.19 | 0.12 | 0.98 |
| 0.5 tbs oregano leaves, crushed | 0.66 | 0.01 | 0.00 | 0.00 | 0.06 | 0.17 | 0.00 |
| 0.5 tbs thyme, crushed | 0.66 | 0.02 | 0.01 | 0.00 | 0.13 | 0.15 | 0.00 |
| 0.5 cup coconut oil | 104.40 | 12.11 | 10.48 | 0.00 | 0.00 | 0.00 | 0.00 |
| 2 tbs chia flour | 17.78 | 1.11 | 0.11 | N/D | N/D | 1.33 | N/D |
| 6 tea bags (green or black) | N/D | N/D | N/D | N/D | N/D | N/D | N/D |
| 1 medium red bell pepper seeded & cut into | ¼- | 2.40 | 0.03 | 0.00 | 0.00 | 0.60 | 0.50 |
| 1 medium leek, white only, chopped | 6.03 | 0.03 | 0.00 | 0.00 | 1.98 | 1.40 | 0.00 |
| 0.5 tsp pepper | 0.39 | 0.00 | 0.00 | 0.00 | 0.01 | 0.09 | N/D |
| 0.5 cup kidney beans | 12.49 | 0.05 | 0.01 | 0.00 | 0.10 | 2.24 | 0.00 |
| 0.5 cup lima beans | 9.73 | 0.03 | 0.01 | 0.00 | 6.52 | 1.82 | 0.00 |
| 0.5 cup lentils, rinsed | 12.76 | 0.04 | 0.01 | 0.00 | 0.22 | 2.21 | 0.00 |
| 0.5 cup chickpeas | 14.94 | 0.24 | 0.02 | 0.00 | 0.64 | 2.50 | 0.00 |
| 0.5 cup great northern beans | 11.60 | 0.04 | 0.01 | 0.00 | 0.20 | 2.07 | N/D |
| 0.5 cup pinto beans | 11.47 | 0.11 | 0.02 | 0.00 | 39.20 | 2.03 | 0.00 |
| 0.5 cup navy beans | 4.33 | 0.05 | 0.01 | 0.00 | 0.78 | 0.83 | N/D |
| 1 can (15 oz) tomatoes, diced | 16.00 | 0.14 | 0.02 | 0.00 | 66.00 | 3.65 | N/D |
| 1 tsp celery seed | 0.87 | 0.06 | 0.00 | 0.00 | 0.36 | 0.09 | 0.00 |
| 4 tbs olive oil | 53.04 | 6.00 | 0.83 | 0.00 | 0.12 | 0.00 | 0.00 |

TABLE 9-continued

| | Ingredient Details | | | | | | |
|---|---|---|---|---|---|---|---|
| Recipe | Ingredient | Calories | Total Fat | Saturated Fat | Cholesterol | Sodium | Carbohy-drates. |
| 1.5 cup bacon, chopped | | 114.51 | 8.84 | 2.91 | 23.28 | 488.95 | 0.30 | 0.00 |
| 1 tsp garlic clove; minced | | 0.46 | 0.00 | 0.00 | 0.00 | 0.05 | 0.10 | 0.00 |
| Total | | 525.27 | 32.73 | 15.63 | 48.95 | 1776.12 | 28.92 | 0.98 |

Antioxidant, as derived from the green tea, was estimated to be equivalent to 291 mg of vitamin C (BY FRSA).

The omega 3 fatty acid content is 689 mg per serving and omega 6 fatty acid content is 233 mg per serving; the ratio of omega 3 to omega 6 is 2.95 to 1.

Costs of Ingredients. The total cost of this Soup was estimated in US dollars based on average U.S. prices in 2014 to be $15.96, or $1.77 per serving.

Example 2

Beef 'N Barley

The Soup of this Example was prepared from the ingredients set forth in Table 10:

TABLE 10

Ingredients:

1.5 tsp salt
1 tsp white pepper
2 lbs beef stew meat
5 tbs olive oil divided
5 tbs coconut oil
3 lg Portobello mushrooms, sliced
2 medium onion chopped
1 medium leek, white only, chopped
2 garlic clove, chopped
16 cups Beef Stock
2 cups butternut squash peeled and cut into 1-inch cubes
2 cups red potato
2 cups red potato
3 large carrot, finely chopped
1.3 cups quick-cooking barley
1 tbs thyme leaves
dash of nutmeg
0.25 cup fresh parsley, chopped
6 bags green tea (12 gm)
2 tbs chia flour
2 cups edamame
1 can (15 oz) diced tomato
1 tsp oregano leaves, crushed
3 tbs butter
0.25 cup milk Preparation: The individual ingredients were prepared according to the teaching herein; e.g. with respect to the size of the food particles and the way that they were prepared in order to optimize the "recognition—appetite stimulation" axis. The Soup was prepared as follows:
1. rinse, dry and season meat with salt and pepper.
2. in a dutch oven or deep pan, heat 3 T of the oil and brown meat remove from pan
3. in the same pan, heat 3 T of extra virgin olive oil and saute the leek, onion, garlic & carrot
4. in 3 cups of stock stir the chia and let sit for at least 10 min.
5. heat remaining stock and steep with tea bags.
6. add all stock, bay leaves, and meat back to pot and simmer for 40 min, then remove tea bags
7. meanwhile, chop the mushrooms, potato, and squash; drizzle with the coconut oil and roast @ 425 for 20-30 or until browned
8. add all remaining ingredients including roasted vegetables to soup and return to boil. Reduce heat, cover and simmer for 20-30 min more or until meat is very tender. Reduce to simmer.
9 Make a rue with the milk butter and flour. Temper the rue then add slowly to soup. Season with salt & pepper
10. Sprinkle with parsley Cooking Times. The following sets forth the times required for the various steps.
Preparation Time: 1 hour
Cooking Time: 2 hours
Inactive Time: 2 hours
Total Time: 3 hours Nutrition Facts: The nutritional content was calculated as the sum of each ingredient as obtained from published information. The nutritional content can also be estimated by the skilled artisan, based upon the components.

Serving size: ⅛ of a recipe (16.1 ounces).
Percent daily values based on the Reference Daily Intake (RDI) for a 2000 calorie diet.

TABLE 11

| Amount Per Serving | amount | % of total calories |
|---|---|---|
| Calories | 601 | (100) |
| Calories From Fat | 277 | 46 |
| Calories From MCT | 73 | 12 |
| Calories From Protein | 146 | 24 |
| Calories From Carbohydrates | 179 | 30 |

TABLE 12

| | Amount | % Daily Value |
|---|---|---|
| Total Fat | 31.5 g | 48 |
| Saturated Fat | 13.7 g | 69 |
| Monounsaturated Fat | 10.7 g | |
| Polyunsaturated Fat | 3.46 g | |
| Trans Fatty Acids | 0.01 g | 16 |
| Fiber | 9.25 g | 37 |
| Cholesterol | 75.6 mg | 25 |
| Sodium | 4470 mg | 186 |

TABLE 12-continued

|  | Amount | | % Daily Value |
|---|---|---|---|
| Potassium | 1300 | mg | 37 |
| Total Carbohydrates | 47.14 | g |  |
| Protein | 36.3 | g | 73 |
| Vitamin A | 8866 | IU | 177 |
| Vitamin C | 2745 | mg | 4576 |
| Calcium | 35.0 | mg | 4 |
| Iron | 160 | mg | 887 |
| Vitamin E | 6.19 | mg | 62 |
| Vitamin D | 0.9 | IU | <1 |
| Thiamin | 11.7 | mg | 785 |
| Riboflavin | 0.37 | mg | 22% |
| Niacin | 0.49 | mg | 2% |
| Vitamin B6 | 9.96 | mg | 498% |
| Folate | 0.86 | µg | <1% |
| Vitamin B12 | 172 | µg | 2868% |
| Pantothenic Acid | 1.34 | mg | 13% |
| Vitamin K | 1.76 | µg | 2% |
| Phosphorus | 69.2 | mg | 7% |
| Magnesium | 379 | mg | 95% |
| Zinc | 89.1 | mg | 594% |
| Copper | 5.53 | mg | 277% |
| Manganese | 0.51 | mg | 26% |
| Selenium | 0.95 | µg | 1% |
| Alcohol | 0 | g |  |
| Caffeine | 0 | mg |  |
| Water | 300 | g |  |

Ingredient Details

The content of the ingredients (entire recipe preparation) is shown below.

TABLE 13

| Recipe Ingredient | Calories | Total Fat | Saturated Fat | Cholesterol | Sodium | Carbohydrates. | Vitamin |
|---|---|---|---|---|---|---|---|
| 1.5 tsp salt | 0.00 | 0.00 | 0.00 | 0.00 | 436.3 | 0.00 | 0.00 |
| 1 tsp white pepper | 0.89 | 0.01 | 0.00 | 0.00 | 0.02 | 0.21 | N/D |
| 2 lbs beef stew meat | 139.05 | 4.25 | 1.48 | 61.43 | 31.05 | 0.00 | 0.00 |
| 5 tbs olive oil divided | 74.59 | 8.44 | 1.17 | 0.00 | 0.17 | 0.00 | 0.00 |
| 5 tbs coconut oil | 73.27 | 8.50 | 7.35 | 0.00 | 0.00 | 0.00 | 0.00 |
| 3 lg portobello mushrooms, sliced | 10.64 | 0.17 | 0.03 | 0.00 | 4.35 | 1.87 | 0.00 |
| 2 medium onion chopped | 11.00 | 0.03 | 0.01 | 0.00 | 1.10 | 2.57 | 0.00 |
| 1 medium leek, white only, chopped | 6.79 | 0.03 | 0.00 | 0.00 | 2.23 | 1.57 | 0.00 |
| 2 garlic clove, chopped | 1.12 | 0.00 | 0.00 | 0.00 | 0.13 | 0.25 | 0.00 |
| 16 cups Beef Stock | 42.72 | 2.22 | 0.55 | 2.08 | 3820.00 | 2.88 | 0.00 |
| 2 cups butternut squash peeled and cut | 15.75 | 0.04 | 0.01 | 0.00 | 1.40 | 4.09 | 0.00 |
| 2 cups red potato | 29.63 | 0.03 | 0.00 | N/D | 2.25 | 6.74 | N/D |
| 3 large carrot, finely chopped | 11.07 | 0.06 | 0.01 | 0.00 | 18.63 | 2.59 | 0.27 |
| 1.3 cups quick-cooking barley | 56.23 | 0.36 | 0.08 | 0.00 | 1.14 | 12.41 | N/D |
| 1 tbs thyme leaves | 1.48 | 0.04 | 0.01 | 0.00 | 0.30 | 0.34 | 0.00 |
| dash of nutmeg | 0.18 | 0.01 | 0.01 | 0.00 | 0.01 | 0.02 | 0.00 |
| .25 cup fresh parsley, chopped | 0.68 | 0.01 | 0.00 | 0.00 | 1.05 | 0.12 | 0.00 |
| 6 bags green tea | N/D | N/D | N/D | N/D | N/D | N/D | N/D |
| 2 tbs chia flour | 20.00 | 1.25 | 0.13 | N/D | N/D | 1.50 | N/D |
| 2 cups edamame | 32.45 | 1.40 | N/D | N/D | 1.77 | 2.53 | N/D |

TABLE 13-continued

| Recipe Ingredient | Calories | Total Fat | Saturated Fat | Cholesterol | Sodium | Carbohydrates. | Vitamin |
|---|---|---|---|---|---|---|---|
| 1 can (15 oz) diced tomato | 16.87 | 0.13 | 0.02 | 0.00 | 141.89 | 3.97 | 2745.56 |
| 1 tsp oregano leaves, crushed | 0.50 | 0.01 | 0.00 | 0.00 | 0.05 | 0.13 | 0.00 |
| 3 tbs butter | 38.18 | 4.32 | 2.74 | 11.45 | 0.59 | 0.00 | 0.00 |
| .25 cup milk | 3.81 | 0.15 | 0.10 | 0.61 | 3.58 | 0.37 | 0.00 |
| .25 cup flour | 14.22 | 0.04 | 0.01 | 0.00 | 0.08 | 2.98 | 0.00 |
| Total | 601.10 | 31.51 | 13.71 | 75.56 | 4467.79 | 47.14 | 2745.83 |

Antioxidant, as derived from the green tea, was estimated to be equivalent to 327 mg of vitamin C BY FRSA.

The omega 3 fatty acid content is 775 mg per serving and omega 6 fatty acid content is 263 mg per serving and the ratio of omega 3 to omega 6 is 2.95 to 1.

Costs of Ingredients. The total cost of this Soup was estimated in US dollars based on average U.S. prices in 2014 to be $16.23, or $12.03 per serving:

Example 3

Creamy Lemon Chicken Chowder

The Soup of this Example was prepared from the ingredients set forth in Table 14:

TABLE 14

| | | Ingredients: |
|---|---|---|
| 4 | cups | chicken breast, diced ¾-inch |
| 2 | cups | onion chopped |
| 3 | medium | carrot, finely chopped |
| 3 | medium | celery chopped |
| 2 | cup | sweet corn kernels |
| 70 | oz | chicken stock or canned chicken broth |
| 2 | | bay leaves |
| 1 | tsp | basil leaves |
| 1 | tsp | thyme, crushed |
| 0.5 | cup | coconut oil |
| 2.5 | tbs | chia flour |
| 6 | | tea bags (12 gm) green tea |
| 1 | small | zucchini or yellow squash, halved lengthwise and cut crosswise into ½-inch pieces |
| 1 | small | leek, white only, chopped |
| 0.5 | cup | extra-virgin olive oil |
| 4 | tbs | butter |
| .25 | tsp | white pepper |
| 0.5 | tsp | salt |
| 1 | cup | peas |
| 1 | cups | edamame |
| 2 | cups | red potato |
| 1 | cup | flour |
| 4 | cups | milk |
| 1 | | lemon zes |

Preparation: The individual ingredients were prepared according to the teaching herein; e.g. with respect to the size of the food particles and the way that they were prepared in order to optimize the "recognition—appetite stimulation" axis. The Soup was prepared as follows:

| | Step description |
|---|---|
| 1 | saute carrots, onion, and celery in the extra virgin olive oil |
| 2 | in stock pot add: half the broth, corn, spices, tea bags |
| 3 | in separate bowl combine chia flour and ½ the stock. stir till well blended and let sit for 10 min |
| 4 | add chia/stock mixture to stock pot |
| 5 | saute chopped kale and leek in coconut oil |
| 6 | add 2 saute mixtures to stock pot and bring to boil just until potatoes are cooked |
| 7 | make a rue with the butter milk and flour. temper with stock then add slowly to soup |
| 8 | simmer for 30 min |
| 9 | remove tea bags before serving |

Cooking Times. The following sets forth the times required for the various steps.

Preparation Time: 1 hour
Cooking Time: 2 hours
Inactive Time: 2 hours
Total Time; 3 hours Nutrition Facts: The nutritional content was calculated as the sum of each ingredient as obtained from published information.

Serving size: ¹/₁₁ of a recipe (17.5 ounces).

Percent daily values based on the Reference Daily Intake (RD) for a 2000 calorie diet.

TABLE 15

| Fraction (per serving) | Calories | % of total |
|---|---|---|
| Total | 510 | 100 |
| From Fat | 284 | 56 |
| From MTC | 85 | 17 |
| From Protein | 102 | 20 |
| From Carbohydrates | 124 | 24 |
| Calories From Alcohol | 0 | 0% |

TABLE 16

| | Amount | % Daily Value |
|---|---|---|
| Total Fat | 32.2 g | 50 |
| Saturated Fat | 15.1 g | 76 |
| Monounsaturated Fat | 11.2 g | |
| Polyunsaturated Fat | 3.5 g | |
| Trans Fatty Acids | 0.08 g | |
| Cholesterol | 56.4 mg | 19 |
| Sodium | 771 mg | 32 |
| Potassium | 846 mg | 24 |
| Total Carbohydrates | 31.6 g | 11 |
| Fiber | 4.9 g | 20 |

TABLE 16-continued

|  | Amount | % Daily Value |
|---|---|---|
| Sugar | 8.92 g | |
| Net Carbohydrates | 26.67 g | |
| Protein | 24.83 g | 50 |
| Vitamin A | 3620 IU | 72 |
| Vitamin C | 1.77 mg | 3 |
| Calcium | 17.0 mg | 2 |
| Iron | 174 mg | 966 |
| Vitamin E | 3.5 mg | 35 |
| Vitamin D | 0.33 IU | <1 |
| Thiamin | 46.6 mg | 3105 |
| Riboflavin | 0.28 mg | 16 |
| Niacin | 0.45 mg | 2 |
| Vitamin B6 | 8.55 mg | 428 |
| Folate | 0.5 μg | <1 |
| Vitamin B12 | 102 μg | 1709 |
| Pantothenic Acid | 0.8 mg | 8 |
| Vitamin K | 1.23 μg | 2 |
| Phosphorus | 37.5 mg | 4 |
| Magnesium | 310 mg | 78 |
| Zinc | 51.9 mg | 346 |
| Copper | 2.08 mg | 104 |
| Manganese | 0.25 mg | 13 |
| Selenium | 0.66 μg | <1 |
| Alcohol | 0 g | |
| Caffeine | 0 mg | |
| Water | 383 g | |

Ingredient Details. The content of the Soup ingredients (with respect to fat, cholesterol, sodium, carbohydrates, and vitaminare shown below.

TABLE 17

| Recipe Ingredient | Calories | Total Fat | Saturated Fat | Cholesterol | Sodium | Carbohydrates. | Vitamin |
|---|---|---|---|---|---|---|---|
| 4 cups chicken breast, diced ¾-inch | 85.02 | 3.38 | 0.92 | 38.18 | 38.18 | 0.00 | N/D |
| 2 cups onion chopped | 8.00 | 0.02 | 0.01 | 0.00 | 0.80 | 1.87 | 0.00 |
| 3 medium carrot, finely chopped | 6.82 | 0.04 | 0.01 | 0.00 | 11.48 | 1.59 | 0.17 |
| 3 medium celery chopped | 1.96 | 0.02 | 0.01 | 0.00 | 9.82 | 0.36 | 0.00 |
| 2 cup sweet corn kernels | 13.12 | 0.12 | 0.02 | 0.00 | 0.45 | 3.09 | 0.00 |
| 70 oz chicken stock or canned chicken broth | 28.39 | 1.01 | 0.28 | 0.00 | 543.01 | 0.67 | 0.00 |
| 2 bay leaves | 0.07 | 0.00 | 0.00 | 0.00 | 0.01 | 0.02 | N/D |
| 1 tsp basil leaves | 0.95 | 0.02 | 0.01 | 0.00 | 0.31 | 0.20 | 1.61 |
| 1 tsp thyme, crushed | 1.08 | 0.03 | 0.01 | 0.00 | 0.22 | 0.25 | 0.00 |
| 0.5 cup coconut oil | 85.42 | 9.91 | 8.57 | 0.00 | 0.00 | 0.00 | 0.00 |
| 2.5 tbs chia flour | 18.18 | 1.14 | 0.11 | N/D | N/D | 1.36 | N/D |
| 6 tea bags (12 gm) green tea | N/D | N/D | N/D | N/D | N/D | N/D | N/D |
| 1 Small zucchini or yellow squash, halved | 3.03 | 0.06 | 0.01 | 0.00 | 1.43 | 0.55 | 0.00 |
| 1 Small leek, white only, chopped | 4.94 | 0.02 | 0.00 | 0.00 | 1.62 | 1.14 | 0.00 |

TABLE 17-continued

| Recipe Ingredient | Calories | Total Fat | Saturated Fat | Cholesterol | Sodium | Carbohydrates. | Vitamin |
|---|---|---|---|---|---|---|---|
| 0.5 cup extra-virgin olive oil | 86.79 | 9.82 | 1.36 | 0.00 | 0.20 | 0.00 | 0.00 |
| 4 tbs butter | 37.02 | 4.19 | 2.65 | 11.10 | 0.57 | 0.00 | 0.00 |
| 0.25 tsp white pepper | 0.16 | 0.00 | 0.00 | 0.00 | 0.00 | 0.00 | 0.04 |
| 0.5 tsp salt | 0.00 | 0.00 | 0.00 | 0.00 | 105.70 | 0.00 | 0.00 |
| 1 cup peas | 9.38 | 0.05 | 0.01 | 0.00 | 13.16 | 1.66 | 0.00 |
| 1 cups edamame | 11.80 | 0.51 | N/D | N/D | 0.64 | 0.92 | N/D |
| 2 cups red potato | 21.55 | 0.03 | 0.00 | N/D | 1.64 | 4.90 | N/D |
| 1 cup flour | 41.36 | 0.11 | 0.02 | 0.00 | 0.23 | 8.67 | 0.00 |
| 4 cups milk | 44.36 | 1.76 | 1.12 | 7.10 | 41.70 | 4.26 | 0.00 |
| Total | 509.41 | 32.22 | 15.12 | 56.38 | 771.15 | 31.57 | 1.77 |

Antioxidant, as derived from the green tea, was estimated to be equivalent to 290 mg of vitamin C BY FRSA.

The Omega 3 fatty acid content is 563 mg per serving and Omega 6 fatty acid content is 191 mg per serving and the ratio of omega 3 to omega 6 is 2.95 to 1.

Costs of Ingredients. The total cost of this Soup was estimated in US dollars based on average U.S. prices in 2014 to be $17.37, or $1.58 per serving.

Example 4

Analysis of Examples 1-3

Examples 1-3 were analyzed statistically and values are set forth in Table 18. Applicant specifically claims as his invention, Soups defined by the average values below (Table 18), Soups defined by the averages plus and minus 2 standard deviations or plus and minus 3 standard deviations.

TABLE 18

|  | avg | min | max | Range avg ± 2 SD | Range avg ± 3 SD |
|---|---|---|---|---|---|
| omega 3 fatty acids (mg) | 675 | 563 | 775 | 462 to 889 | 356 to 995 |
| omega 6 fatty acids (mg) | 229 | 191 | 263 | 157 to 301 | 120 to 338 |
| Ratio of omega 3/6 (mg) | 2.95 |  |  |  |  |
| Cholesterol (mg) | 60.3 | 49 | 75.60 | 32.9 to 87.8 | 19.2 to 102 |
| Calories From Carbohydrates | 138 | 111 | 179 | 65.8 to 210 | 29.7 to 246 |
| % of total | 25.0 | 21.0 | 30.0 | 15.8 to 34.2 | 11.2 to 38.8 |
| Calories From Protein | 124.33 | 102 | 146 | 80.32 to 168 | 58.3 to 190 |
| % of total | 22.7 | 20.0 | 24.0 | 18.0 to 27.3 | 15.7 to 29.6 |
| Calories From MTC | 87.3 | 73.0 | 104 | 56.1 to 119 | 40.4 to 134 |
| % of total | 16.3 | 12.0 | 20.0 | 8.25 to 24.4 | 4.21 to 28.5 |
| Calories From Fat | 283 | 277 | 289 | 271 to 295 | 265 to 301 |
| % of total | 52.3 | 46.0 | 56.0 | 41.32 to 63.4 | 35.8 to 68.9 |
| Calories Total | 545 | 510 | 601 | 448 to 643 | 399 to 692 |
| Cal per ml | 1.12 | 1.02 | 1.31 | 0.78 to 1.46 | 0.61 to 1.63 |
| fiber (gm) | 7.68 | 4.90 | 9.25 | 2.85 to 12.52 | 0.43 to 14.9 |
| vol (ounces) | 17.3 | 16.10 | 18.2 | 15.13 to 19.41 | 14.1 to 20.5 |
| Antioxidant (mg vit C equivalent by FRSA) | 302 | 290 | 327 | 260 to 345 | 239 to 366 |
| Total Fat (g) | 32.1 | 32.7 | 31.5 | 30.9 to 33.3 | 30.3 to 33.9 |
| Saturated Fat (g) | 14.8 | 15.6 | 13.7 | 12.8 to 16.8 | 11.8 to 17.8 |
| Monounsaturated Fat (g) | 10.9 | 11.2 | 10.7 | 10.4 to 11.4 | 10.1 to 11.7 |

TABLE 18-continued

|  | avg | min | max | Range avg ± 2 SD | Range avg ± 3 SD |
|---|---|---|---|---|---|
| Polyunsaturated Fat (g) | 3.55 | 3.7 | 3.46 | 3.31 to 3.78 | 3.20 to 3.90 |
| Trans Fatty Adds (g) | 0.03 | 0.08 | 0.00 | −0.06 to 0.12 | −0.10 to 0.16 |

Example 5

Manufacturing of Food Products§

Food scientists and chefs are given the requirements of Formulations 1-20 and asked to produce recipes for Soups. Each formulation is prepared in each of the forms set forth as Soups S-100-S195. The maximum solid food particle size is to be 20 cm$^3$ and optionally, in a length (i.e. the longest dimension) of less than about 5 cm. Food substances are to be cut, where possible or convenient, in a manner that preserves the recognizable appearance of the food stuffs—for example, techniques other than grating or shredding are desirable. Cutting is also performed in a manner that allows for easy mastication with the limitations of the poor dentition status in this population.

After each of the Soups are made, they are analyzed for content to confirm that the specifications have each been achieved.

Example 6

Packaging Food Products

Each of the Soups made according to Example 1-Example 3 and Example 5 are packaged in a single serving, easy open container. On the outside of the container, a label is placed containing a large print name and a graphic representation of the contents as taught above (see "labeling"). The container is shaped like a soup bowl that has a lid. The container also has a graphic depicting the Soup or a ingredient of the Soup.

Example 7

Nutritional Plans

A team of nutrition specialists convene to make recommendations concerning the use of Soups and Packaged Food Product as manufactured in Example 5 and Example 6. Detailed nutritional plans are established for dementia subjects as a whole, and as subgroups based on other factors (e.g. age, weight, gender, severity of dementia, etc.).

Example 8

Food Product Kits

Several of the containers of Soup manufactured as described in Example 5 and Example 6 are assembled in a kit, i.e. packaged as a single unit of purchase. Included in the kit is a written description of the nutritional plan (e.g., as taught herein).

Example 9

Efficacy Testing

This is an interventional, randomized, safety and efficacy parallel assignment, multi-site trial to test compliance and efficacy of nutritional plan with the present nutritional products.

Subjects are assessed by their capacity to consent by a psychiatrist or neurologist independent of this study. Subjects who are determined to have capacity sign consent. For subjects determined to lack capacity, consent is obtained from their surrogate. Subjects lacking in capacity must nonetheless provide verbal assent to participate in this study. After informed consent is obtained, subjects are screened for eligibility to participate in the study. Screening comprises of medical history, physical exam, neurological exam, and a MMSE (mini mental state examination, or alternatively, Hodkinson abbreviated mental test score or the General Practitioner Assessment Of Cognition).

Eligible subjects are not asked to stop any medication they may currently be on before the study begins. At baseline, medical history, physical exam, cognitive tests are obtained. An ECG and a panel consisting of CBC, electrolytes, liver and renal function, and baseline nutritional status tests are drawn at the screening visit. Clinical information is obtained from the identified caregiver. The study nutritional product kits (containing a nutritional plan) are dispensed to the subjects that are randomized to the "treatment arm" at baseline. Follow up visits at months 3, 6, 9, and 12 months require physical exam and some cognitive measures. At Month 6 and 12, neurological exams are performed. Adverse events are collected at each visit. Compliance with the nutritional plan is assessed at months 3, 6, 9, and 12 months. Clinical information is obtained from the caregiver at each visit.

Eligibility
Ages Eligible for Study: 50 Years to 90 Years
Genders Eligible for Study: Both
Accepts Healthy Volunteers: No
Criteria
Inclusion Criteria:
Consenting individuals as defined by IRB guidelines
NINCDS/ADRDA criteria for probable AD
Community dwelling
Age: greater than or equal to 50 years
MMSE between 12 and 26, inclusive
Stable medical condition for 3 months prior to screening visit
Stable doses of (non excluded) medications with central nervous system activity for 4 weeks prior to the screening visit (For cholinesterase inhibitors there should be no plan of dose escalation)
Physically acceptable for this study as confirmed by medical history, physical exam, neurologic exam and clinical laboratory tests Study partner to accompany subject to all scheduled visits and complete informant-based assessments.
Fluent in English
Modified Hachinski<4
CT or MRI since onset of memory impairment demonstrating absence of clinically significant focal lesion (One lacune in a non-critical brain region is acceptable)
Able to complete baseline assessments
6 years of education, or work history sufficient to exclude mental retardation
Presence of a family and/or professional caregiver willing and able to participate in all aspects of this study
Exclusion Criteria:
Active liver disease or persistent elevation in serum transaminase
Severe renal disease
—Hx of diabetes mellitus (both insulin-dependent and non-insulin-dependent) or blood glucose >150 mg/dl
Active neoplastic disease (skin tumors other than melanoma are not exclusionary; subjects with stable prostate cancer or other stable cancers may be included at the discretion of the PI (Sano))
Use of another investigational agent within 2 months of the screening visit
History of clinically significant stroke
Current evidence or history in the past 2 years of seizures, head injury with loss of consciousness and/or immediate confusion after the injury
Current DSM-5 criteria-based diagnosis for major psychiatric disorder including psychosis, major depression, bipolar disorder, alcohol or substance abuse.
Blindness, deafness, language difficulties or any other disability which may interfere with testing ability
In female subjects, no history of menopause
Use of medications containing aluminum hydroxide, including anti-ulcer antacids such as Alternagel, Amphojel, Alu-tab, Maalox and MylantaThe citations provided herein are hereby incorporated by reference for the cited subject matter.
Patients with clinically significant laboratory abnormalities
Patients receiving investigational pharmacologic agents
Patients with known allergies to any of the food components in the testing samples
Primary Outcome Measures:
Clinician Interview-Based Assessment of Change Plus Caregiver Input (CIBIC-Plus) global score at baseline, 4, 12, 28 and 52 weeks.
The changes from baseline to weeks 28 & 52 in the Alzheimer's Disease Cooperative Study Activities of Daily Living Inventory modified for severe dementia (ADCS-ADLsev) assessed at 0, 4, 12, 28 weeks.
Secondary Outcome Measures:
Severe Impairment Battery [Time Frame: Baseline, 4, 12, 28, 52 weeks]
Mini-Mental State Examination [Time Frame: Baseline, 4, 12, 28, 52 weeks]
Functional Assessment Staging [Time Frame: Baseline, 4, 12, 28, 52 weeks]
Global Deterioration Scale [Time Frame: Baseline, 4, 12, 28, 52 weeks]
Behavioral Pathology in Alzheimer's Disease-Frequency Weighted [Time Frame: Baseline, 4, 12, 28, 52 weeks]
Memory and Behavior Problems Checklist [Time Frame: Baseline, 4, 12, 28, 52 weeks]
All secondary outcomes scored at baseline, 4, 12, and 28 weeks [Time Frame: Baseline, 4, 12, 28, 52 weeks]

Results

After six months and one year, the intervention group showed improvements (compared to the control group) in each primary and secondary outcomes. The intervention group showed higher levels of albumin, pre-albumin, iron, zinc, and beta-carotene than the control group. The same response in BMI, MNA, and triceps skinfold. Mortality was lower in the intervention group, as was the number of infectious events and the days in bed.

Example 10

Case Study

This is a case study as of observed and written by the inventor of the present invention. The subject is an 87 year old woman with a diagnosis of dementia. Until October of 2012, she had lived and managed on her own in the home that she shared with her husband and where she raised her children. She had been widowed for the last 23 years, and had functioned independently during that entire time. Her children had noticed mild memory changes starting in her mid-eighties but, up until that point, they appeared appropriate to her age, and she continued to maintain a relatively normal level of functioning, with some scaling back of activities, such as driving, that were self imposed and appropriate to her age related capabilities.

After an episode of syncope in September, 2012, she was evaluated at a local hospital, and a CT scan showed evidence of brain changes that were consistent with normal aging, which was expected. The syncope had no apparent cause, and she was released from the hospital. She maintained a good health and quality of life status despite diagnoses of osteoporosis, congestive heart failure, hypercholesterolemia and dementia. She attended to her doctor's appointments regularly.

Within a short period of time, however, she began to forget meals, and as a result of this, her weight and nutritional status began to decline. So much so, that between October of 2012 and January of 2013, she lost nearly 12 pounds. It was at this time that her children also noticed a more marked level of decline which included missed doses of medication, more isolative behaviors, and an inability to cook for herself. Multiple fixes began to be incorporated during this time, including the hiring of caregivers, and the regular delivery of meals. Despite these fixes, meals continued to be an issue as her appetite and interest in food declined, a common experience referred to as "the dwindles".

Even with the regular meal deliveries, there was only limited success in providing adequate nutrition. It was further observed by the inventor herein that proper nutrition could sometimes be self-delivered/administered when the food consisted of soup. Moreover, the following were observed to further strengthen and make more consistent the positive outcomes associated with self-administered soup:

Portion Size: On multiple occasions, it was noted that the subject was able to finish at least 10 of the 14 ounces portion size provided in a bowl. Larger volume portions appeared to be less well-received (e.g. more likely to be initially refused or she would consume less than she might otherwise consume when served in a 14 ounce portion.

Recognition. The subject viewed the soup with no suspicion, and accepted both the content and portion. She easily accepted the container given its bowl like appearance and familiar shape. The spoon also appeared more acceptable, in contrast to a situation where multiple utensils are given where the subject would typically fumble with the utensils, as if to be contemplating their use.

Packaging. A number of observations lead to a conclusion that in order to provide effective nutrition to this subject, a special packaging would be required to accommodate her challenges, e.g. arthritis, declining nutritional status that made her quite thin and weak, and the mental confusion. Packaging that did not require tools to open, instructions to read, or physical strength or dexterity produced more favorable results (e.g. compliance).

Food Preparation. The subject had a diminished ability to use appliances and family members expressed concerned about the danger involved in the subject cooking. The subject was able to operate the microwave oven to heat soup.

Simplicity. It was observed that the subject had difficulty with instructions, so much so that there was a strong aversion to anything with an appearance of complexity. Recognizing this, soup provided without simple instructions that she was able to generally follow. The family reported success with these instructions and expressed comfort that she was managing this process on her own. Remote reminders appeared to reinforce the instructions.

General Applicability. The observations regarding the subject as made by the physician/inventor are believed by him to be consistent with observations of other subjects with Alzheimer's and related dementias. Moreover, the optimized features (as set forth above), when combined, unexpectedly result in an effective food product that can have a remarkable impact on a subjects nutritional states, weight maintenance, quality of life, independence, and mental function.

Accordingly, through insight of the inventor, it has been discovered that Soups of the present invention not only meet the nutritional demands of dementia subjects, but provide a vehicle that imparts enhanced compliance for self-administration. Moreover, such enhanced compliance can now be utilized to deliver anti-dementia therapy in the form of a nutritional soup, e.g. a soup tailored with antioxidants, a ketosis-inducing formulation, an anti-insulin resistance formulation, and/or anti-dementia agents.

What is claimed is:

1. A product comprising a reversibly closable container and a soup, wherein the soup is in the container and has:
    a. a total volume of 200 to 2000 ml;
    b. at least one of a vegetable component and a meat component;
    c. 300 to 2500 calories;
    d. a macronutrient caloric distribution that is:
        i. 20% to 80% fat;
        ii. 15.7% to 29.6% protein;
        iii. 10% to 65% carbohydrate; and
        iv. about 2% to about 40% medium chain triglycerides,
    e. optionally one or more antioxidants in a total amount of at least 100 mg equivalents of vitamin C by free radical scavenging activity (FRSA);
    f. optionally omega 3 fatty acids in an amount of at least 100 mg; and
    g. optionally a means for extending the stability of the product.

2. The product of claim 1 comprising omega 3 fatty acids in an amount of 100 to 2000 mg, and comprising antioxidants in a total amount of 100 mg to 500 mg equivalents of vitamin C by FRSA.

3. The product of claim 1 wherein the product, when provided daily to a subject with dementia, results in a benefit to the subject, wherein the benefit is a positive impact on one or more of subject nutritional status, subject quality of life; subject disease course; subject demand for assistance from a care giver; and subject compliance.

4. The product of claim 1, wherein the macronutrient caloric distribution is 30% to 80% fat.

5. The product of claim 1, wherein the macronutrient caloric distribution comprises 30% or less fat.

6. The product of claim 1, wherein the macronutrient caloric distribution is 10% to 25% protein.

7. The product of claims 1, wherein the macronutrient caloric distribution is 10% to 50% carbohydrate.

8. The product of claim 1, wherein the macronutrient caloric distribution is 30-65% fat.

9. The product of claim 1, wherein the soup further comprises:
    a. at least 4 mg vitamin B6;
    b. at least 75 µg vitamin B12;
    c. at least 3 mg vitamin E
    d. at least 15 mg iron;
    e. at least 200 mg magnesium; and
    f. at least 10 mg thiamin.

10. The product of claim 2, wherein the soup has less than 1,500 mg sodium per 2000 calories.

11. The product of claim 2, wherein the soup comprises calcium in an amount of at least 1000 mg per 2000 calories.

12. The product of claim 1, wherein the soup further comprises solid food particles, wherein less than 20% by weight of the total solid food particles is provided by solid food particles having a volume greater than about 20 $cm^3$ and optionally wherein the solid food particles have a maximum length of about 5 cm.

13. The product of claim 1 wherein the soup comprises omega 3 fatty acids present in an amount of about 350 mg to about 1000 mg, wherein the macronutrient caloric distribution is 35% to 70% fat; 15% to 30% protein; 10% to 40% carbohydrate; and 4% to 30% medium chain triglycerides, wherein the total calories are at least 400 and optionally less than 1,000, wherein the antioxidant is present in an amount of 200 to 600 mg of vitamin C equivalents by FRSA, and wherein the total volume is 300 to 600 mls.

14. The product of claim 1, wherein the container is an easy-open container and the container is optionally microwavable.

15. The product of claim 12, wherein the container is a cup or bowl and optionally wherein the container comprises a handle.

16. A kit comprising a plurality of products of claim 1 and a nutritional plan comprising written instructions for use of the kit by a subject with dementia.

17. The kit of claim 16 further comprising an event monitoring system.

18. A method of treating a subject with dementia comprising providing the kit of claim 17 and directing the subject to comply with the nutritional plan.

19. The product of claim 1, wherein the soup is a small particle Soup.

20. The product of claim 12, wherein the container is a metered container.

21. A product comprising a reversibly closable container and a soup, wherein the soup is in the container and has:
    a. a total volume of 200 to 2000 ml;
    b. at least one of a vegetable component and a meat component;
    c. 300 to 2500 calories;
    d. a macronutrient caloric distribution that is:
        i. 20% to 80% fat;
        ii. 10% to about 25% protein;

iii. 10% to 65% carbohydrate; and
iv. about 2% to about 40% medium chain triglycerides,
e. optionally one or more antioxidants in a total amount of at least 100 mg equivalents of vitamin C by free radical scavenging activity (FRSA);
f. optionally omega 3 fatty acids in an amount of at least 100 mg; and
g. optionally a means for extending the stability of the product.

22. The product of claim 1 wherein the soup further comprises fiber in an amount of at least about 10 grams of fiber per 1000 calories.

23. The product of claim 1 wherein the carbohydrate macronutrient comprises simple carbohydrates and wherein less than 10% of the calories are provided by the simple carbohydrates.

24. The product of claim 1, wherein the macronutrient caloric distribution is 30% to 65% fat, 15.7% to 25% protein, and 10% to 50% carbohydrate and wherein the soup has a water content of 60% to 95% (weight/weight).

* * * * *